US008951533B2

(12) United States Patent
Yiannikouris et al.

(10) Patent No.: US 8,951,533 B2
(45) Date of Patent: Feb. 10, 2015

(54) CLAY INTERLACED YEAST COMPOSITIONS AND METHODS OF UTILIZING THE SAME

(71) Applicant: Alltech, Inc., Nicholasville, KY (US)

(72) Inventors: Alexandros Yiannikouris, Lexington, KY (US); Ursula Anne Thielen, Lexington, KY (US)

(73) Assignee: Alltech, Inc., Nicholasville, KY (US)

( * ) Notice: Subject to any disclaimer, the term of this patent is extended or adjusted under 35 U.S.C. 154(b) by 63 days.

(21) Appl. No.: 13/685,294

(22) Filed: Nov. 26, 2012

(65) Prior Publication Data

US 2013/0084356 A1 Apr. 4, 2013

Related U.S. Application Data

(60) Division of application No. 12/856,407, filed on Aug. 13, 2010, now Pat. No. 8,318,475, which is a continuation-in-part of application No. 12/687,833, filed on Jan. 14, 2010, now abandoned.

(60) Provisional application No. 61/144,620, filed on Jan. 14, 2009.

(51) Int. Cl.
*A61K 36/06* (2006.01)
*A01N 63/04* (2006.01)
*A23K 1/16* (2006.01)
*A23K 1/00* (2006.01)
*A23K 1/175* (2006.01)
*A23K 1/18* (2006.01)
*A23L 1/03* (2006.01)
*A23L 1/30* (2006.01)
*A23L 1/304* (2006.01)
*A23L 2/52* (2006.01)
*C12H 1/044* (2006.01)
*C12H 1/056* (2006.01)
*C12N 1/16* (2006.01)
*A01K 1/015* (2006.01)

(52) U.S. Cl.
CPC . *A23K 1/16* (2013.01); *A23K 1/009* (2013.01); *A23K 1/1756* (2013.01); *A23K 1/1826* (2013.01); *A23L 1/0305* (2013.01); *A23L 1/3018* (2013.01); *A23L 1/304* (2013.01); *A23L 2/52* (2013.01); *A61K 36/06* (2013.01); *C12H 1/0408* (2013.01); *C12H 1/0424* (2013.01); *C12N 1/16* (2013.01); *A01K 1/0154* (2013.01)
USPC .................................................. 424/195.16

(58) Field of Classification Search
None
See application file for complete search history.

(56) References Cited

U.S. PATENT DOCUMENTS

| 6,045,834 | A  | * | 4/2000  | Howes et al. ............. 426/2 |
| 6,344,221 | B1 |   | 2/2002  | Evans |
| 7,740,861 | B2 |   | 6/2010  | Ostroff |
| 2003/0007982 | A1 | | 1/2003  | Surai |
| 2005/0281781 | A1 | | 12/2005 | Ostroff |

FOREIGN PATENT DOCUMENTS

| CN | 1158554      | 9/1997  |
| CN | 1372814      | 10/2002 |
| CN | 1843154      | 10/2006 |
| WO | 98/34503     | 8/1998  |
| WO | 2007/021262  | 2/2007  |

OTHER PUBLICATIONS

Maignan et al., Effect of Clay Minerals on Microorganism Metabolism. Comptes Rendus du Congress National des Societes Savantes, Section des Sciences (1973). Volume date 1971, 96 (3), 193-209. (no English abstract provided).

Bauman Mirela et al: "Natural zeolite clinoptilolite increases the concentrations of sphingoid bases in the yeast *Yarrowia lipolytica*", Journal of Basic Microbiology, vol. 41, No. 1, 2001, pp. 7-16, XP002693564, ISSN: 0233-111X.

Naunyn-Schmiedeberg's Archives of Pharmacology, "Abstracts", Springer, Berlin, DE, vol. 374, No. 4, Dec. 20, 2006, pp. 317-346, XP019471887, ISSN: 1432-1912.

Kolosova A et al: "Substances for reduction of the contamination of feed by mycotoxins—a review", World Mycotoxin Journal, Wageningen Academic Publishers, Netherlands, vol. 4, No. 3, Jan. 1, 2011, pp. 225-256, XP009167730, ISSN: 1875-0710.

(Continued)

*Primary Examiner* — Chris R Tate
*Assistant Examiner* — Randall Winston
(74) *Attorney, Agent, or Firm* — Valerie L. Calloway; Merchant & Gould, PC

(57) ABSTRACT

The present invention relates to compositions comprising yeast cells and/or yeast cell components and methods for producing and utilizing the same. In particular, the invention provides novel yeast comprising altered cell wall structure (e.g., clay and/or clay component(s) integrated (e.g., interlaced) into cell wall(s) and/or cell wall(s) comprising altered glucan:mannan ratio), methods of producing the same, compositions comprising and/or derived from the same, and methods of using the same (e.g., to sequester and/or adsorb bacteria and toxins). Compositions and methods of the invention find use in a variety of applications including dietary (e.g., admixing with feedstuffs or otherwise feeding to animals), therapeutic, prophylactic (e.g. admixing with bedding sources and/or other materials that come into contact with animals, usage during food and beverage processing and manufacture, and usage during filtration of liquids) as well as research applications.

7 Claims, 9 Drawing Sheets

(56) References Cited

OTHER PUBLICATIONS

Hagler W.M., Jr., 1991, In: Mycotoxins, Cancer and Health, (Bray G. and Ryan D. eds.) Lousiana State University Press, Baton Rouge, LN, USA.

Phillips T.D., Clement B.A., and Park D.L., 1994, Approaches to reduction of aflatoxin in foods and feeds, In: The toxicology of aflatoxins: Human health, veterinary agriculture significance (Eaton L.D. and Groopman J.D. eds.), Academic Press, New York, NY, USA, pp. 383-406.

Lemke et al., Development of a multi-tiered approach to the in vitro prescreening of clay-based enterosorbents, Animal Feed Science and Technology, 93 (2001) 17-21.

El-Nezami, H., Kankaanpaa, P., Salminen, S., & Ahokas, J. (1998). Ability of dairy strains of lactic acid bacteria to bind a common food carcinogen, aflatoxin B1. Food and Chemical Toxicology, 36(4), 321-326.

Yoon, Y. H., & Baek, Y. J. (1999). Aflatoxin binding and antimutagenic activities of Bifidobacterium bifidum HY strains and their genotypes. Korean Journal of Dairy Science, 21(4), 291-298.

Yiannikouris A et al., A novel technique to evaluate interactions between *Saccharomyces cerevisiae* cell wall and mycotoxins application to zearalenone, 2003, Biotechnology Letters, vol. 25, pp. 783-789.

Zhang and Xu, Adsorptive Properties of β-D-Glucans Extracted from Spent Brewer Yeast Cell Wall against Zearalenone, College of Food Science and Technology, Southern Yangtze University, Wuxi 214036, China, 2006, vol. 27, No. 4, pp. 75-78.

Galvagno and Cerrutti, Aumento de la actividad panificante de levaduras comerciales por aplicación de condiciones de estrés durante su propagación, Revista Argentina de Microbiologia (2004) 36: 41-46.

\* cited by examiner

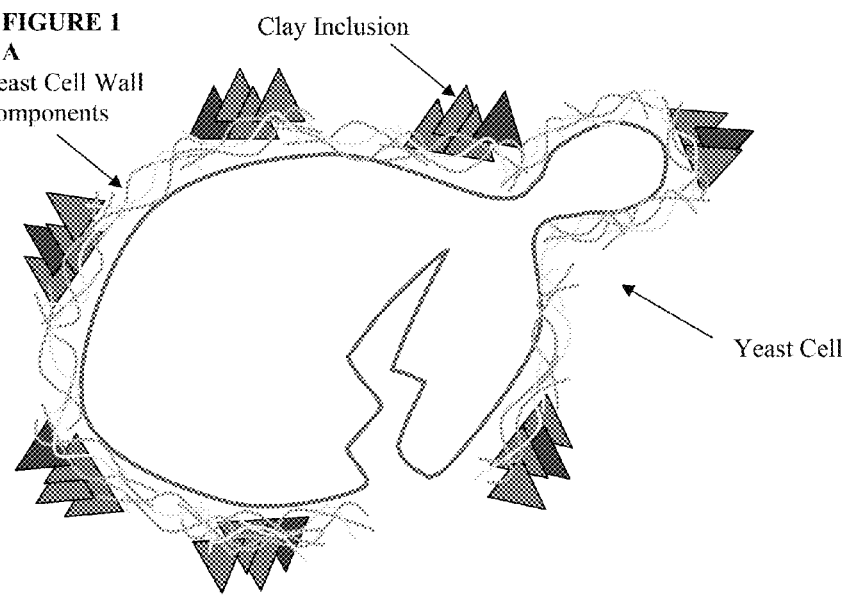
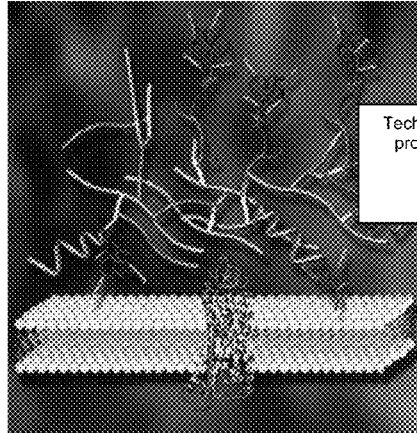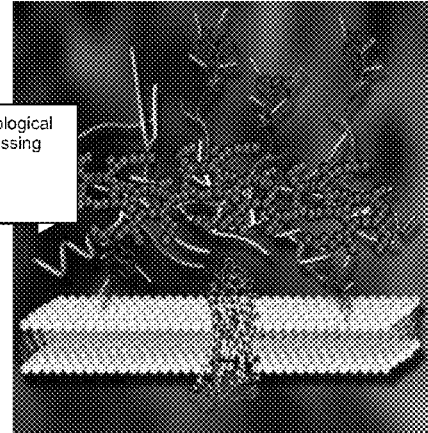
FIGURE 1
A Yeast Cell Wall Components — Clay Inclusion — Yeast Cell
B Cell grown without clay / Cell grown with clay — Technological processing — Cell wall, Plasmic membrane of the cell
- (1→3)-β-D-glucans
- (1→6)-β-D-glucans
- (1→4)-α-D-glucans
- mannoproteins
- glucophospho-inositiol chain
- N-acetylglucosamine chain (chitin)
- Clay

FIGURE 3

| Sample | Glucan (%) | Mannan (%) | Ratio G/M | Protein (%) | Remnant (%) | Adsorption ZEARALENONE (%) |
|---|---|---|---|---|---|---|
| YCW only | 45.52 ± 0.54 | 41.29 ± 0.62 | 1.01 | 12.38 | 0.81 | 6.91 ± 2.19 |
| YCW + 0.5% | 42.68 ± 0.49 | 35.70 ± 0.20 | 1.20 | 14.34 | 7.28 | 45.64 ± 5.30 |
| YCW + 1.0% | 42.69 ± 0.39 | 31.67 ± 0.37 | 1.35 | 15.83 | 9.81 | 73.55 ± 2.98 |
| YCW + 2.0% | 38.24 ± 0.28 | 26.34 ± 0.17 | 1.45 | 19.89 | 15.53 | 79.33 ± 2.24 |

FIGURE 4

| Sample | Glucan (%) | Mannan (%) | Ratio G/M | Adsorption ZEARALENONE (%) | Adsorption AFLATOXIN B1 (%) | Ash Content (%) |
|---|---|---|---|---|---|---|
| YCW only | 32.457 ± 0.19 | 25.92 ± 0.28 | 1.25 | 69.34 ± 0.58 | 2.65 ± 0.55 | 2.76 |
| YCW + 1.0% | 39.93 ± 0.26 | 22.29 ± 0.23 | 1.79 | 80.33 ± 0.28 | 40.73 ± 3.30 | 7.58 |
| YCW + 2.0% | 36.14 ± 0.20 | 20.97 ± 0.12 | 1.72 | 85.89 ± 1.02 | 53.70 ± 1.97 | 10.33 |

FIGURE 6

| Exp/Batch # | 08-036 | 09-002 |
|---|---|---|
| Material ID | 0.5.% Smectite ClYCW Spray-dried | 0.5.% Smectite ClYCW Spray-dried |
| % ash | 21.59 | 20.26% |
| %C | 37.82 | 37.43 |
| %H | 5.3 | 5.1745 |
| %N | 3.75 | 5.15 |
| %Protein | 23.46 | 32.14 |
| Total Plate Count (cfu/g) | $9.35 \times 10^4$ | - |
| | 1.79 (5hrs) | 0.14 (0hr) |
| | 4.07 (9hrs) | 0.60 (3hrs) |
| % alcohol | 4.72 (11hrs) | 1.64 (6hrs) |
| | - | 2.90 (9hrs) |
| | - | 4.82 |
| % glucose | 27.5 | 28.2 |
| % mannose | 19.4 | 16.1 |

FIGURE 7

| Yeast | Clay (1%, smectite) | Enzyme hydrolysis | Adsorption (%) | |
|---|---|---|---|---|
| | | | AFB1 | ZEA |
| ADY (YCW only) | - | + | 6.9 ± 4.5 | 39.3 ± 2.4 |
| ADY (#08-036) | + | + | 85.3 ± 5.3 | 57.9 ± 1.1 |
| (#09-002) | | | 99.8 ± .02 | 55.1 ± 1.1 |

FIGURE 8

| Yeast | Clay (0.5%, Smectite) | Enzyme hydrolysis | Adsorption (%) | |
|---|---|---|---|---|
| | | | AFB1 | ZEA |
| ADY | + | + | 75.4 ± 13.2 | 69.2 ± 1.2 |

FIGURE 9

| Yeast | Clay (1%, MBB02) | Enzyme hydrolysis | Adsorption (%) | |
|---|---|---|---|---|
| | | | AFB1 | ZEA |
| Levapan | + | + | 93.8 ± 6.9 | 56.7 ± 0.7 |
| Levapan | - | - | 6.7 ± 2.7 | 40.3 ± 0.7 |
| DCL | + | + | 89.3 ± 4.5 | 51.3 ± 1.6 |
| DCL | - | - | 4.7 ± 5.4 | 48.6 ± 1.4 |
| ADY | + | + | 91.6 ± 5.0 | 68.7 ± 0.4 |
| ADY | - | + | 6.1 ± 2.8 | 58.7 ± 0.9 |
| ADY | - | - | 5.8 ± 3.7 | 39.5 ± 0.9 |

US 8,951,533 B2

CLAY INTERLACED YEAST COMPOSITIONS AND METHODS OF UTILIZING THE SAME

This application is a Divisional of U.S. patent application Ser. No. 12/856,407 filed Aug. 13, 2010, which is a Continuation-In-Part Application of U.S. patent application Ser. No. 12/687,833 filed Jan. 14, 2010, which claims priority to U.S. Provisional Application 61/144,620 filed Jan. 14, 2009, each of which is hereby incorporated by reference in its entirety.

FIELD OF THE INVENTION

The present invention relates to compositions comprising yeast cells and/or yeast cell components and methods for producing and utilizing the same. In particular, the invention provides novel yeast comprising altered cell wall structure (e.g., clay and/or clay component(s) integrated (e.g., interlaced) into cell wall(s) and/or cell wall(s) comprising altered glucan:mannan ratio), methods of producing the same, compositions comprising and/or derived from the same, and methods of using the same (e.g., to sequester and/or adsorb bacteria and toxins). Compositions and methods of the invention find use in a variety of applications including dietary (e.g., admixing with feedstuffs or otherwise feeding to animals), therapeutic, prophylactic (e.g. admixing with bedding sources and/or other materials that come into contact with animals, usage during food and beverage processing and manufacture, and usage during filtration of liquids) as well as research applications.

BACKGROUND OF THE INVENTION

Fungi are ubiquitous worldwide, and inconspicuous as they are most commonly microscopically small. Mycotoxins are secondary metabolites secreted by fungi. Mycotoxins are toxic and/or carcinogenic compounds produced by various fungal species that grow on various agricultural commodities. Examples of mycotoxins, include but are not limited to aflatoxins, fumonisins, ochratoxin A, deoxynivalenol (a.k.a. "DON" or "vomitoxin"), patulin, and zearalenone. Myotoxins are often produced in cereal grains as well as forages before, during and after harvest. Some mycotoxins are lethal, some cause identifiable diseases or health problems, some weaken the immune system without producing symptoms specific to that mycotoxin, some act as allergens or irritants, and some have no known effect on animals or humans. The greatest economic impact of mycotoxin contamination is felt by crop and poultry producers, as well as food and feed producers. Mycotoxins can appear in the food chain as a result of fungal infection of plant products, and can either be eaten directly by humans, or introduced by contaminating livestock feedstuff(s). Mycotoxins contaminate organic materials (e.g. bedding) as well as water, and greatly resist decomposition during digestion so they remain in the food chain in edible products (e.g. meat, eggs and dairy products). No region of the world escapes mycotoxins and their negative impact on animal and human health. The evolution of global trading of feedstuffs increases the chances that blends of grains will result in combinations of mycotoxins in a given diet and that unusual and unsuspected mycotoxins will be present in a given region regardless of its climate condition.

Strategies used to avoid mycotoxin occurrence involve controlling elements that permit mycotoxin production, controlling mold growth, as well as practicing quality control of food and feeds via adequate sampling, detection and quantification methodology. However, mycotoxin contamination is unavoidable.

In order to reduce the negative effects of mycotoxins, inorganic materials such as clays, bentonites, and aluminosilicates, known for their adsorptive properties, have historically been added to feedstuffs. Feedstuff-additives, in large quantities, sequester some mycotoxins in the gastrointestinal tract of the animal and minimize their toxic effects. However, additives hinder the absorption of many beneficial nutrients that are important to animals such as vitamins, minerals, and amino acids thereby decreasing the nutrient density of the diet. Moreover, feedstuff additives, particularly in animal feces, have an extremely detrimental environmental impact.

Chemical agents such as acids, bases (e.g., ammonia, caustic soda), oxidants (e.g., hydrogen peroxide, ozone), reducing agents (e.g., bisulphites), chlorinated agents and formaldehyde, have been used to degrade mycotoxins in contaminated feeds, particularly aflatoxins (See, e.g., Hagler 1991; Phillips et al 1994; Lemke et al 2001). However, these techniques are not efficient, are expensive, generate a significant amount of chemical waste, and are generally unsafe.

Certain strains of lactic acid bacteria, propionibacteria and bifidobacteria have cell wall structures that bind mycotoxins (See, e.g., Ahokas et al 1998; El-Nemazi et al 1998; Yoon et al 1999) and limit their bioavailability in the animal body. However, these biological processes are generally slow, produce toxic metabolites, and are inefficient.

SUMMARY OF THE INVENTION

In some embodiments, the present invention provides a yeast cell comprising a yeast cell wall comprising clay or a clay component interlaced into the yeast cell wall. In some embodiments, the yeast cell is cultivated in a cell culture medium comprising clay. In some embodiments, the clay is a mineral clay or synthetic clay belonging to the silicate group. In some embodiments, the clay is selected from a zeolite, a bentonite, an aluminosilicate, a montmorillonite, a smectite, a kaolinite, an organoclay and mixtures thereof. In some embodiments, the clay is an aluminosilicate clay. In some embodiments, the amount of clay in the cell culture medium is from about 0.125% to about 4.0%. In some embodiments, the amount of clay in the cell culture medium is from 0.125% to 4.0%. In some embodiments, the amount of clay in the cell culture medium is from about 0.5% to about 2.0%. In some embodiments, the amount of clay in the cell culture medium is from 0.5% to 2.0%. In some embodiments, the yeast is selected from *Saccharomyces, Candida, Kluyveromyces, Torulaspora* and combinations thereof. In some embodiments, the yeast is *Saccharomyces cerevisiae*.

In some embodiments, the present invention provides composition comprising a clay or clay component interlaced yeast cell wall extract. In some embodiments, the clay or clay component interlaced yeast cell wall extract is derived from a yeast cell cultivated in growth medium comprising a clay. In some embodiments, glass beads and a bead beater are utilized to prepare the yeast cell wall extract. In some embodiments, enzymatic treatment is utilized to prepare the yeast cell wall extract. In some embodiments, the clay or clay component interlaced yeast cell wall extract is added to a feedstuff. In some embodiments, the feedstuff is selected from a Total Mixed Ration (TMR), a forage, a pellet, a concentrate, a premix, a coproduct, grain, distiller grain, molasses, fiber, fodder, grass, hay, kernel, leaves, meal, solubles, and a supplement. In some embodiments, the clay or clay component interlaced yeast cell wall extract is added to organic material. In some embodiments, the clay or clay component interlaced yeast cell wall extract is added to water. In some embodiments, a liquid is filtered through the clay or clay component interlaced yeast cell wall extract. In some embodiments, the liquid is a juice, water, beer or wine. In some embodiments, the composition is formulated for feeding to any member of Kingdom Animalia. In some embodiments, the member of Kingdom Animalia is selected from avian, bovine, porcine, equine, ovine, and caprine, piscines, shellfish, camelids, feline, canine, and rodent species. In some embodiments, the clay or clay component interlaced yeast cell wall extract sequester one or more mycotoxins. In some embodiments, the mycotoxin is selected from Aflatoxins, Zearalenone, Trichothecenes, Fumonisins, and Ochratoxins. In some embodiments, the mycotoxin is selected from of acetoxyscirpenediol, acetyldeoxynivalenol, acetylnivalenol, acetylneosolaniol, acetyl T-2 toxin, extended to all aflatoxins, aflatoxin B1, B2, G1 and G2, aflatrem, altenuic acid, alternariol, austdiol, austamide, austocystin, avenacein +1, beauvericin +2, bentenolide, brevianamide, butenolide, calonectrin, chaetoglobosin, chaetocin, chaetomin, citrinin, citreoviridin, cochliodinol, cytochalasins, cyclopiazonic acid, deacetylcalonectrin, deactylneosolaniol, deoxynivalenol diacetate, deoxynivalenol monoacetate, diacetoxyscirpenol, destruxin B, emestrin, enniatins, extended to all ergot alkaloids toxins and endophytes such as ergine, ergocornine, ergocristine, ergocryptine, ergometrine, ergonine, ergosine, ergotamine, ergovaline, lysergol, lysergic acid, and related epimers, fructigenin +1, fumagilin, fumonisins, fumonisins A1, A2, B1 and B2 and B3, fusarenon-X, fusarochromanone, fusaric acid, fusarin, gliotoxin, HT-2 toxin, hyalodendrin, ipomeanine, islanditoxin, isofumigaclavines A and B, lateritin +1, leptosin, lycomarasmin +1, malformin, maltoryzine, moniliformin, monoacetoxyscirpenol, mycophenolic acid, neosolaniol, nivalenol, NT-1 toxin, NT-2 toxin, extended to all ochratoxins, oosporein, oxalic acid, paspalitrem A and B, patulin, penicillic acid, penitrem, phomopsins, PR-toxin, roridin E, roquefortine A and B, rubratoxin, rubroskyrin, rubrosulphin, rugulosin, sambucynin +1, satratoxins, F, G, H, scirpentriol, sirodesmin, slaframine, sporidesmin, sterigmatocystin, swainsonine, T-1 toxin, T-2 toxin, tenuazoic acid, triacetoxyscirpendiol extended to all trichothecenes, trichodermin, trichothecin, trichoverrins, trichoverrols, tryptoquivalene, verrucarin, verruculogen, verticillins, viopurpurin, viomellein, viriditoxin, wortmannin, xanthocillin, yavanicin+1, zearalenols, zearalanones, zearalenone, α, β, zearalanone, α, β, zeranol and subfamilies and/or derivatives of the same, and/or conjugates.

In some embodiments, the present invention provides a compositions comprising a clay or clay component interlaced yeast cell wall extract, wherein the clay or clay component interlaced yeast cell wall extract is present in an amount effective to sequester mycotoxins. For example, in some embodiments, the clay or clay component interlaced yeast cell wall extract is present in an amount of about 0.0125% to about 10% by weight of a feedstuff. In some embodiments, the clay or clay component interlaced yeast cell wall extract is present in an amount of about 0.0125% to about 4.0% by weight of a feedstuff. The present invention is not limited by the type of feedstuff.

In some embodiments, the present invention provides a method for reducing bioavailability of mycotoxins to an animal or human comprising: (a) providing: (i.) a composition comprising a clay or clay component interlaced yeast cell wall extract, and (ii) a material consumed by animal or human; (b) incorporating the clay or clay component interlaced yeast cell wall extract into the material to produce a clay or clay component interlaced yeast cell wall extract incorporated material; and (c) allowing the animal or human to consume the clay or clay component interlaced yeast cell wall extract incorporated material. In some embodiments, the material is a feedstuff. In some embodiments, about 0.0125% to about 0.4% by weight of the composition comprising a clay or clay component interlaced yeast cell wall extract is added to a feedstuff. In some embodiments, the material is bedding. In some embodiments, the about 0.0125% to about 99.0% of the composition comprising a clay or clay component interlaced yeast cell wall extract is added by weight to the bedding. In some embodiments, material is a liquid. In some embodiments, about 0.0125% to about 99.0% of the composition comprising a clay or clay component interlaced yeast cell wall extract is added by weight to the liquid. In some embodiments, the animal is selected from of avian, bovine, porcine, equine, ovine, and caprine, piscines, shellfish, camelids, feline, canine, and rodent species. In some embodiments, the composition comprising a clay or clay component interlaced yeast cell wall extract sequesters one or more types of mycotoxins. In some embodiments, the mycotoxins are Aflatoxins, Zearalenone, Trichothecenes, Fumonisins, Ochratoxins, or combinations thereof. In some embodiments, the present invention further provides incorporating an additional agent into the clay or clay component interlaced yeast cell wall extract incorporated material, wherein the agent is selected from an esterase, epoxidase, yeast and/or bacterial strain.

In some embodiments, the present invention provides a method of producing a commercial-scale quantity of clay or clay component interlaced yeast cell wall extract comprising: (a) providing: (i) yeast starter culture and (ii) yeast cell culture media, wherein the yeast cell culture media comprises the required nutrients for yeast growth and a clay or clay component; (b) introducing the yeast starter culture into the yeast cell culture media; (c) incubating the yeast in an industrial-scale fermenter under conditions configured to allow yeast growth, wherein the yeast incorporate the clay or clay component into the yeast cell wall during growth; (d) adding anti-foaming agent to the fermenter; (e) lysing the clay or clay component interlaced yeast cells walls; and (f) separating the clay or clay component interlaced yeast cells walls from the other yeast components. In some embodiments, the yeast is selected from *Saccharomyces, Candida, Kluyveromyces, Torulaspora* or combinations thereof. In some embodiments, the clay is a mineral clay or synthetic clay belonging to the silicate group. In some embodiments, the clay is a zeolite, a bentonite, an aluminosilicate, a montmorillonite, a smectite, a kaolinite, an organoclay or mixture thereof. In some embodiments, the clay is an aluminosilicate clay. In some embodiments, the amount of clay in the cell culture medium is from about 0.125% to about 4.0%. In some embodiments, the amount of clay in the cell culture medium is from about 0.5% to about 2.0%. In some embodiments, the amount of clay in the cell culture medium is from 0.125% to 4.0%. In some embodiments, the amount of clay in the cell culture medium is from 0.5% to 2.0%. In some embodiments, the industrial-scale fermenter is between one thousand and five million liters. In some embodiments, the anti-foaming agent is added to alleviate effects of the clay on the incubation process. In some embodiments, the anti-foaming agent is a nonsilicone molecular defoamer, oil-based defoamer, powder defoamer, water-based defoamer, silicone based defoamer, polyethylene glycol-based defoamer, polypropylene glycol-based defoamer, or alkyl polyacrylates. In some embodiments, the anti-foaming agent is a nonsilicone molecular defoamer. In some embodiments, the lysing comprises glass beads, a bead beater and/or enzymatic treatment.

DESCRIPTION OF THE DRAWINGS

FIG. 1 shows A) a depiction of a yeast cell with clay and/or clay components interlaced into the yeast cell wall, and B) a comparative description of (a) the yeast cell wall of a yeast cell cultivated in the absence of clay and (b) the yeast cell wall of a yeast cell grown/cultivated in the presence of clay.

FIG. 3 provides characteristics of yeast cell wall extracts prepared utilizing glass beads and a minibead beater from yeast cells: cultivated in the absence of clay (Yeast Cell Wall "YCW" only), yeast cells cultivated in the presence of 0.5% clay (YCW +5%), yeast cells cultivated in the presence of 1% clay (YCW +1.0%), and yeast cells cultivated in the presence of 2.0% clay. Additionally, the percentages of adsorption of the mycotoxin zearalanone for each of the samples.

FIG. 4 provides characteristics of yeast cell wall extracts prepared utilizing protease cutting from yeast cells cultivated in the absence of clay (YCW only), yeast cells cultivated in the presence of 1% clay (YCW +1.0%), and yeast cells cultivated in the presence of 2.0% clay.

FIG. 6 shows the composition of two batches of CIYCW produced at a semi-industrial scale.

FIG. 7 shows sequestration efficacy results obtained with the yeast cell wall semi-industrial scale, with and without smectite clay and having been or not extracted with enzyme hydrolysis. The level of inclusion of the sequestrants product for AFB1 and ZEA were respectively of 0.1 and 0.4% in the reaction medium that was maintained at a constant pH of 4.0. The assay was performed under orbital agitation during 90 min at 37° C. and the amount of bound toxin evaluated using HPLC equipped with a fluorescent detector.

FIG. 8 shows sequestering efficacy results obtained with the yeast cell wall production with smectite clay and having been extracted with enzyme hydrolysis. The level of inclusion of the sequestrants product for AFB1 and ZEA were respectively of 0.1 and 0.4% in the reaction medium that was maintained at a constant pH of 4.0. The assay was performed under orbital agitation during 90 min at 37° C. and the amount of bound toxin evaluated using HPLC equipped with a fluorescent detector.

FIG. 9 shows adsorption results obtained with the different yeast cell wall coming from three strains grown with or without clay MBB02 and having been or not extracted with enzyme hydrolysis. The level of inclusion of the sequestrants product for AFB1 and ZEA were respectively of 0.1 and 0.4% in the reaction medium that was maintained at a constant pH of 4.0. The assay was performed under orbital agitation during 90 min at 37° C. and the amount of bound toxin evaluated using HPLC equipped with a fluorescent detector.

DEFINITIONS

Figure 2:
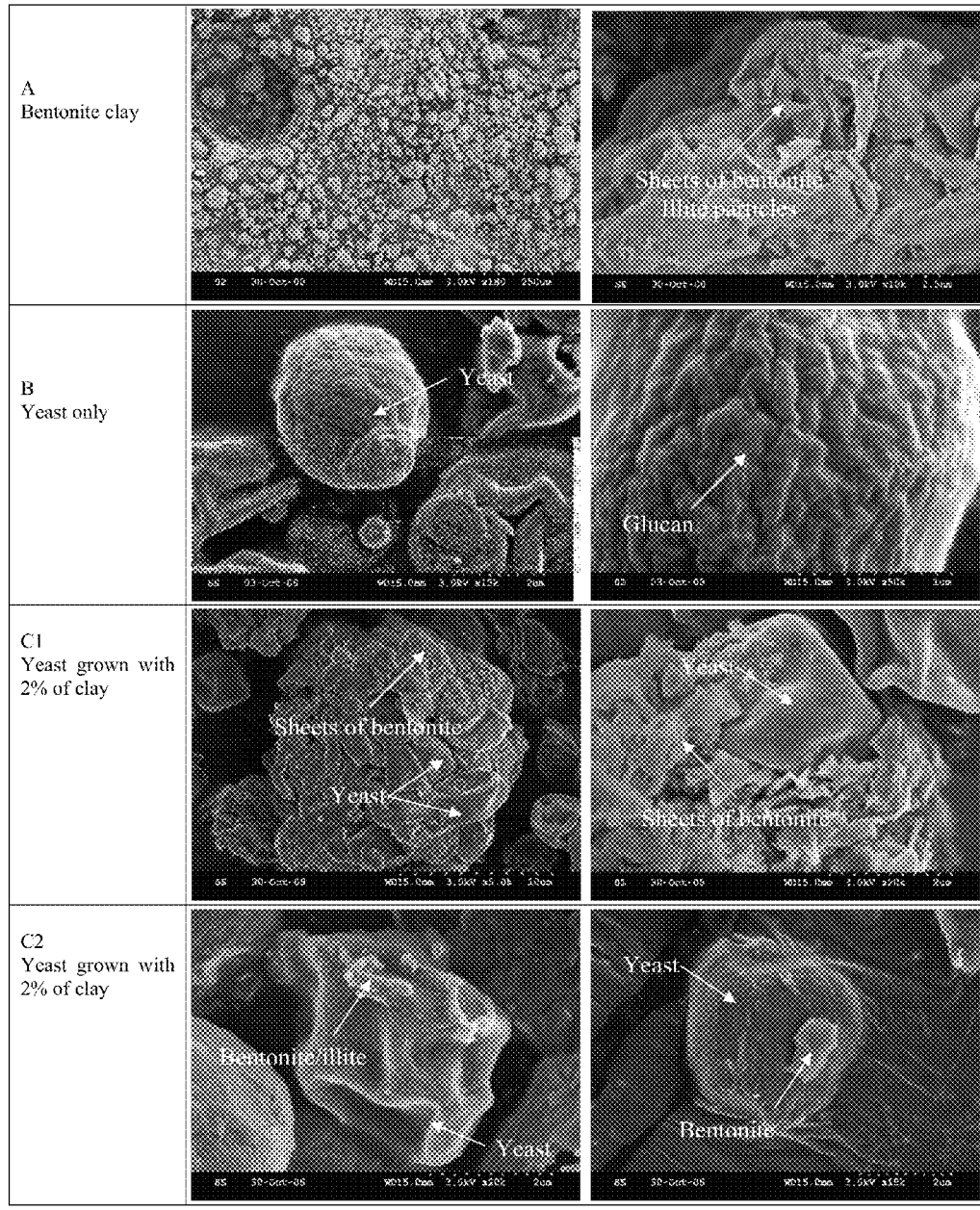
FIG. 2 shows a scanning electron micrograph of (A) a bentonite clay (Fluka); (B) yeast cells cultivated in the absence of clay and a close-up of the glucan portion of the yeast cell wall; (C1) yeast cells cultivated in the presence of 2% bentonite clay with detail of a conglomerate formation of several yeast cells trapped in the lamellar structure of bentonite; (C2) yeast cells cultivated in the presence of 2% bentonite clay with detail of an inclusion of the clay directly in the yeast cell wall structure.
Figure 5:
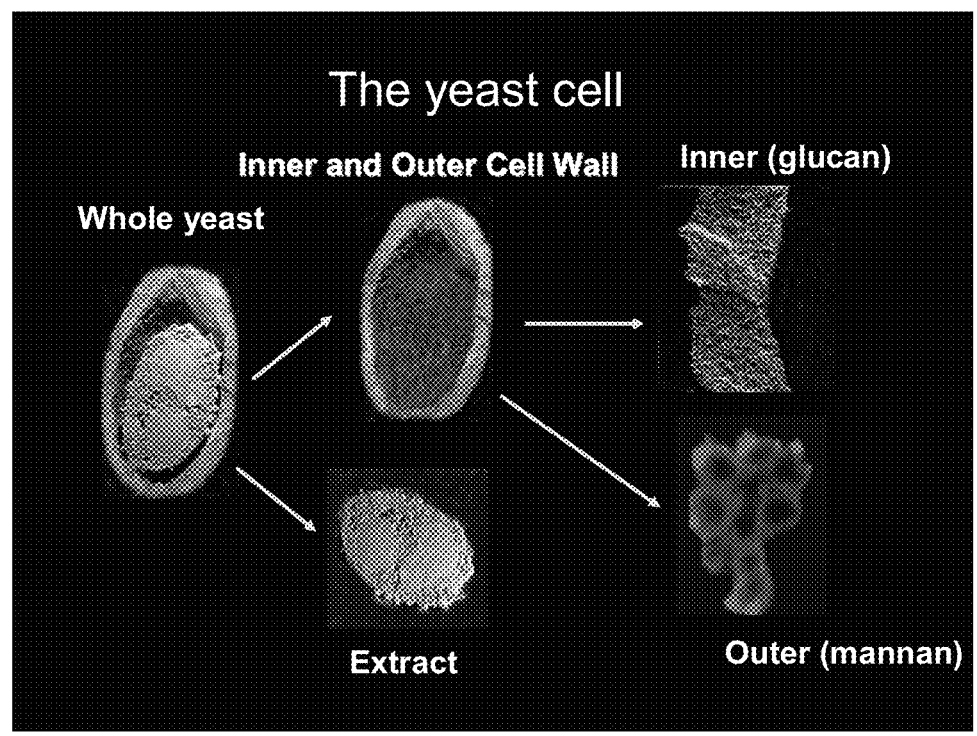
FIG. 5 depicts the anatomy of a yeast cell.

As used herein, the term "yeast" and "yeast cells" refers to eukaryotic microorganisms classified in the kingdom Fungi, having a cell wall, cell membrane and intracellular components. Yeasts do not form a specific taxonomic or phylogenetic grouping. Currently about 1,500 species are know; it is estimated that only 1% of all yeast species have been described. The term "yeast" is often taken as a synonym for *S. cerevisiae*, but the phylogenetic diversity of yeasts is shown by their placement in both divisions Ascomycota and Basidiomycota. The budding yeasts ("true yeasts") are classified in the order Saccharomycetales. Most species of yeast reproduce asexually by budding, although some reproduce by binary fission. Yeasts are unicellular, although some species become multicellular through the formation of a string of connected budding cells known as pseudohyphae, or false hyphae. Yeast size can vary greatly depending on the species, typically measuring 3-4 μm in diameter, although some yeast can reach over 40 μm.

As used herein, the term "yeast cell wall" also referred to as "YCW" refers to the cell wall of a yeast organism that surrounds the plasmic membrane and the intracellular components of the yeast. Yeast cell wall includes both the outer layer (mainly mannan) and the inner layer (mainly glucan and chitin) of the yeast cell wall. A function of the cell wall is to provide structure and protect the yeast interior (its metabolic activity center). Signaling and recognition pathways take place in the yeast cell wall. The composition of yeast cell wall varies from strain to strain and according to growth conditions of yeast.

As used herein, the term "yeast cell wall extract" refers to the yeast cell wall of yeast that has been ruptured or "lysed" (e.g., during a rupture and lysing stage) and separated from the soluble intracellular components of the yeast cell.

The term "isolated" when used in relation to a yeast cell wall, as in "an isolated yeast cell wall" or "isolated clay integrated yeast cell wall" or "isolated yeast cell wall comprising altered glucan:mannan structure" refers to a yeast cell wall or component thereof that is identified and separated from at least one component with which it is ordinarily associated in its natural source. Thus, an isolated yeast cell wall is such present in a form or setting that is different from that in which it is found in nature (e.g., that is separate from intracellular components of yeast). In contrast, non-isolated yeast cell wall is a yeast cell wall or component thereof found in the state they exist in nature. In some embodiments, isolated yeast cell wall is used to describe yeast cell wall extract.

As used herein, the term "purified" or "to purify" refers to the removal of components from a sample. For example, yeast cell walls or yeast cell wall extracts are purified by removal of non-yeast cell wall components (e.g., plasmic membrane and/or yeast intracellular components); they are also purified by the removal of contaminants or other agents that are not yeast cell wall. The removal of non-yeast cell wall components and/or non-yeast cell wall contaminants results in an increase in the percent of yeast cell wall or components thereof in a sample. In another example, yeast cell walls comprising clay or clay components integrated/interlaced into the yeast cell wall are purified by the removal of non-yeast cell wall components (e.g., plasmic membrane and/or yeast intracellular components), thereby the percent of yeast cell wall comprising clay or clay components integrated/interlaced into the cell wall is increased in a sample.

As used herein, the term "concentrated yeast cell wall extract" refers to yeast cell wall extract that is concentrated via one or more procedures (e.g., by drying (e.g., during a drying and concentrating stage)). In another example, a concentrated yeast cell wall extract is a yeast cell wall preparation or yeast cell wall extract preparation that is purified by removal of non-yeast cell wall components.

As used herein, the terms "modified yeast" and "altered yeast" refer to yeast cultivated in a way that alters the composition, structure and/or function of the yeast (e.g., that alters the composition, structure and/or function of the yeast cell wall (e.g., a yeast cell wall comprising an altered glucan:mannan ratio and/or clay/clay component integrated/interlaced into the yeast cell wall that functions differently than a yeast cell wall without altered glucan:mannan ratio and/or non-clay or non-clay component integrated/interlaced yeast cell wall).

As used herein, the term "modified yeast cell wall" refers to yeast cell wall of modified or altered yeast.

As used herein, the term "modified yeast cell wall extract" refers to yeast cell wall extract of modified or altered yeast.

As used herein, the term "concentrated modified yeast cell wall extract" as used herein refers to concentrated yeast cell wall extract derived from modified or altered yeast, for example, in U.S. Pat. No. 6,045,834.

As used herein, the terms "clay interlaced yeast," "clay integrated yeast," "clay component interlaced yeast," "clay component integrated yeast" refer to yeast grown or cultivated in the presence of clay or clay components that has incorporated or interlaced clay or clay components into the yeast cell wall. Clay or clay component interlaced yeast and is a specific type of modified yeast.

As used herein, the term "interlaced" as in "clay interlaced yeast cell wall extract," clay component interlaced yeast cell wall extract," or the like refers to the integration of clay or clay component into yeast cell wall. Although a mechanism is not necessary to practice the invention and the invention is not limited to any particular mechanism of action, in some embodiments, interlacing of clay or clay component into yeast cell wall occurs during yeast growth (e.g., after its asexual reproductive cycle (budding) (e.g., as a daughter cell grows and forms its yeast cell wall network, clay or clay component integrates into the yeast cell)). In one example, elongation of the chains of glucan and/or chitin provide integration site(s) involved in the integration of the clay or clay component during budding, resulting in the daughter cell comprising clay or clay component integrated into its cell wall. In another example, the macromolecular clay structure traps yeast cell(s) in its lamellar network, wherein the yeast cell proceeds through budding, further integrating clay or clay component into the yeast cell wall. Yeast cell wall integrated/interlaced clay and/or clay component(s) remain integrated/interlaced in yeast cell wall post cell wall extraction.

As used herein, the terms "clay interlaced yeast cell wall," "clay component integrated yeast cell wall," "clay component interlaced yeast cell wall," and "clay integrated yeast cell wall" refer to yeast cell wall of yeast grown or cultivated in the presence of clay that has incorporated or interlaced clay or clay components into the yeast cell wall.

As used herein, the terms "clay interlaced yeast cell wall extract," "clay component interlaced yeast cell wall extract," "clay integrated yeast cell wall extract," and "clay component integrated yeast cell wall extract" refer to yeast cell wall extract of yeast (e.g., wherein the yeast from which the cell wall extract is made are grown or cultivated in the presence of clay) that has incorporated or interlaced clay or clay components into the yeast cell wall (also abbreviated CIYCW).

As used herein, the terms "concentrated interlaced yeast cell wall extract" and "concentrated integrated yeast cell wall extract" refer to concentrated yeast cell wall extract of yeast grown or cultivated in the presence of clay that has incorporated or interlaced clay or clay components into the yeast cell wall.

As used herein, the term "in vivo" refers to studies and/or experiments conducted within a living organism, occurring within a biological organism.

As used herein, the term "in vitro" refers to an artificial environment outside the living organism and to biological processes or reactions that would normally occur within an organism but are made to occur in an artificial environment. In vitro environments can comprise of, but are not limited to, test tubes and cell culture.

As used herein, the term "high-performance liquid chromatography" and the term "HPLC" refer to a form of liquid chromatography to separate compounds. The compounds are dissolved in solution. Compounds are separated by injecting a plug of the sample mixture onto the column. HPLC instruments comprise a reservoir of mobile phase, a pump, an injector, a separation column, and a detector. The presence of analytes in the column effluent is recorded by quantitatively detecting a change in refractive index, UV-VIS absorption at a set wavelength, fluorescence after excitation with a suitable wavelength, or electrochemical response.

As used herein, the term "scanning electron microscopy" and the term "SEM" refer to a type of electron microscope that images the sample surface by scanning it with a high-energy beam of electrons in a raster scan pattern. The electrons interact with the atoms that make up the sample producing signals that contain information about the sample's surface topography, composition and other properties such as electrical conductivity.

As used herein, the term "fixation agent" refers to a chemical that is capable of fixing one substance to another in order to "fix", stabilize, or otherwise preserve the substance in its current form to prevent the substance from degrading or otherwise changing. Often, fixation agents are used in scanning electron microscopy (abbreviated as SEM) to prepare the sample. Primary fixation agent: as used herein, the terms "primary fixation agent" refers to the first fixation agent used to "fix" a substance. Secondary fixation agent: as used herein, the terms "secondary fixation agent" refers to the second fixation agent used to "fix" a substance. Tertiary fixation agent: as used herein, the terms "tertiary fixation agent" refers to the third fixation agent used to "fix" a substance.

As used herein, the term "analyte" refers to an atom, a molecule, a grouping of atoms and/or molecules, a substance, or chemical constituent. An analyte, in and of itself cannot be measured, rather, aspects or properties (physical, chemical, biological, etc.) of the analyte can be determined using an analytical procedure, such as HPLC. For example, one cannot measure a "chair" (analyte-component) in and of itself, but, the height, width, etc. of a chair can be measured. Likewise, one cannot measure a mycotoxin but can measure the mycotoxin fluorescence that is related to its concentration.

As used herein, the term "signal" is used generally in reference to any detectable process that indicates that a reaction has occurred (for example, binding of antibody to antigen). Signals can be assessed qualitatively as well as quantitatively. Examples of types of "signals" include, but are not limited to, radioactive signals, fluorimetric signals or colorimetric product/reagent signals.

As used herein, the term "bioavailability" refers to the fraction of a molecule or component that is available to an organism or reaches the systemic circulation. When a molecule or component is administered intravenously, its bioavailability is 100%. However, when a molecule or component is administered via other routes (such as orally), its bioavailability decreases (due to incomplete absorption and first-pass metabolism).

As used herein, the term "absorb" refers to the process by which a material "takes in" or "sucks up" another substance. For example, "absorption" may refer to the process of absorbing or assimilating substances into cells or across the tissues and organs through diffusion or osmosis (e.g. absorption of nutrients by the digestive system or absorption of drugs into the blood stream).

As used herein, the term "adsorption" refers to a process that occurs when a material is sequestered by, and/or accumulates on the surface of, a solid or a liquid (sequestrant and/or adsorbent) (e.g. thereby forming a film of molecules or atoms (the adsorbate)).

As used herein, the term "sequester" and/or the term "sequestration" refers to physical association (e.g., via docking or encasement) of two or more entities that come into contact with one another (e.g., thereby forming a stable complex). Exemplary forms of associations include, but are not limited to, hydrogen bonding, coordination, and ion pair formation. Sequestration interactions may involve a variable number of chemical interactions (e.g., chemical bonds) depending on the stereochemistry and geometry of each entity (e.g., further defining the specificity of the sequestration). When two or more entities are sequestered they may be sequestered by way of chemical bonds, but may also be associated via charge or other type of interactions.

As used herein, the term "sequestration agent" and/or "sequestering agent", refers to an entity that is capable of inducing or otherwise being involved with a sequestration and/or forming a complex with a second entity.

As used herein, the term "sorption" refers to both adsorption and absorption.

As used herein, the term "effective amount" refers to the amount of a composition (e.g., comprising a yeast cell, yeast cell wall or modified yeast cell wall component of the invention) sufficient to effect beneficial or desired results. An effective amount can be administered and/or combined with another material in one or more administrations, applications or dosages and is not intended to be limited to a particular formulation or administration route.

As used herein, the term "digest" refers to the conversion of food, feedstuffs, or other organic compounds into absorbable form; to soften, decompose, or break down by heat and moisture or chemical action.

As used herein, "digestive system" refers to a system (including gastrointestinal system) in which digestion can or does occur.

As used herein, the term "feedstuffs" refers to material(s) that are consumed by animals and contribute energy and/or nutrients to an animal's diet. Examples of feedstuffs include, but are not limited to, Total Mixed Ration (TMR), forage(s), pellet(s), concentrate(s), premix(es) coproduct(s), grain(s), distiller grain(s), molasses, fiber(s), fodder(s), grass(es), hay, kernel(s), leaves, meal, soluble(s), and supplement(s).

As used herein, the term "animal" refers to those of kingdom Animalia. This includes, but is not limited to livestock, farm animals, domestic animals, pet animals, marine and freshwater animals, and wild animals.

As used herein, the terms "administration" and the term "administering" refer to the act of giving a substance, including a drug, prodrug, or other agent, or therapeutic treatment to a subject (e.g., a subject or in vivo, in vitro, or ex vivo cells, tissues, and organs). Exemplary routes of administration can be through the eyes (ophthalmic), mouth (oral), skin (topical or transdermal), nose (nasal), lungs (inhalant), oral mucosa (buccal), ear, rectal, vaginal, by injection (e.g., intravenously, subcutaneously, intratumorally, intraperitoneally, etc.) and the like.

As used herein, the term "co-administration" and the term "co-administering" refer to the administration of at least two agent(s) or therapies to a subject and/or material (e.g., feedstuff). Co-administration of two or more agents or therapies can be concurrent, or a first agent/therapy can be administered prior to a second agent/therapy.

As used herein, the term "treatment" refers to the improvement and/or reversal of the symptoms of disease (e.g., mycotoxicosis). The term "treatment" refers to both therapeutic treatment and prophylactic or preventative measures. For example, subjects that may benefit from treatment with compositions and methods of the present invention include those already with a disease and/or disorder (e.g., mycotoxicosis) as well as those in which a disease and/or disorder is to be prevented (e.g., using a prophylactic treatment of the present invention).

As used herein, the term "at risk for disease" refers to a subject that is predisposed to experiencing a particular disease. This predisposition may be genetic (e.g., a particular genetic tendency to experience the disease, such as heritable disorders), or due to other factors (e.g., age, weight, environmental conditions, exposures to detrimental compounds present in the environment, etc.).

As used herein, the term "disease", the term "infection" and the term "pathological condition or response" refer to a state, signs, and/or symptoms that are associated with an impairment of the normal state of a living animal or of any of its organs or tissues that interrupts or modifies the performance of normal functions, and may be a response to environmental factors (such as malnutrition, industrial hazards, or climate, including mycotoxicosis), specific infective agents (such as worms, bacteria, or viruses), to inherent defect of the organism (such as various genetic anomalies), or combinations of these and other factors.

As used herein, the term "mycotoxicosis" refers to a condition in which mycotoxins pass the resistance barriers of the human or animal body. Mycotoxicosis can be considered either an infection or a disease and may have a deleterious effect on those afflicted.

As used herein, the term "mycotoxin" refers to toxic and/or carcinogenic compound(s) produced by various fungal species.

As used herein, the term "suffering from disease" refers to a subject (e.g., an animal or human subject) that is experiencing a particular disease and is not limited to any particular signs or symptoms, or disease.

As used herein, the term "toxic" refers to any detrimental, deleterious, harmful, or otherwise negative effect(s) on a subject, a cell, or a tissue as compared to the same cell or tissue prior to the contact or administration of the toxin/toxicant.

As used herein, the term "acid" as used herein refers to any chemical compound that can donate proton(s) and/or accept electron(s). Acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

As used herein, the term "base" refers to any chemical compound that can accept proton(s) and/or donate electron(s) or hydroxide ions. Bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

As used herein, the term "salt" refers to compounds that may be derived from inorganic or organic acids and bases. Examples of salts include, but are not limited to, acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

As used herein, the term "pharmaceutical composition" refers to the combination of an active agent (e.g., a composition comprising a viable yeast cell, yeast cell wall, or modified yeast cell wall component of the invention) with a carrier, inert or active, making the composition especially suitable for diagnostic or therapeutic use in vitro, in vivo or ex vivo.

As used herein, the term "pharmaceutically acceptable" and the term "pharmacologically acceptable" refer to compositions that do not substantially produce more known adverse reactions than known beneficial reactions.

As used herein, the term "antifoaming agent" refers to an additive used to prevent formation of foam or is added to break foam already formed. An "antifoaming agent" also referred to as "antifoamer" or "defoamer" refers to an additive which reduces the surface tension of a solution or media or emulsion or broth in fermenters because of aeration or agitation, thus inhibiting or modifying the formation of a foam. Commonly used agents are insoluble oils, dimethyl polysiloxanes and other silicones, certain alcohols such as stearyldecanol, octal decanol, sulphonates, stearates and glycols.

As used herein, the term "cell" refers to an autonomous self-replicating unit that may exist as functional independent unit of life (as in the case of unicellular organism, e.g. yeast), or as sub-unit in a multicellular organism (such as in plants and animals) that is specialized into carrying out particular functions towards the cause of the organism as a whole. There are two distinct types of cells: prokaryotic cells and eukaryotic cells.

As used herein, the term "eukaryote" refers to organisms whose cells are organized into complex structures enclosed within membranes. "Eukaryotes" are distinguishable from "prokaryotes." The term "prokaryote" refers to organisms that lack a cell nucleus or other membrane-bound organelles. The term "eukaryote" refers to all organisms with cells that exhibit the typical characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals.

As used herein, the term "cell culture" refers to any in vitro culture of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "cell reproduction" refers to a process of cell multiplication having three primary stages. The first stage of cell reproduction involves the replication of the "parental cell's DNA. The second stage is the separation of the duplicated DNA into two equally sized groups of chromosomes. The third stage is the physical division of entire cells, usually called cytokinesis. Cell reproduction is more complex in eukaryotes than in other organisms. Non-eukaryotic cells such as bacterial cells reproduce by binary fission, a process that includes DNA replication, chromosome segregation, and cytokinesis. Eukaryotic cell reproduction either involves mitosis or a more complex process called meiosis. Mitosis and meiosis are sometimes called the two "nuclear division" processes. Binary fission is similar to eukaryotic cell reproduction that involves mitosis. Both lead to the production of two daughter cells with the same number of chromosomes as the parental cell. Meiosis is used for a special cell reproduction process of diploid organisms. It produces four special "daughter cells" (gametes) which have half the normal cellular amount of DNA. A male and a female gamete can then combine to produce a zygote, a cell which again has the normal amount of chromosomes.

As used herein, the term "yeast reproduction" refers to the reproduction cycle of yeast, which have asexual and sexual reproductive cycles, however the most common mode of vegetative growth in yeast is asexual reproduction by "budding" or "fission" with a "daughter cell" that is formed on the "parent cell". The nucleus of the parent cell splits into a daughter nucleus and migrates into the daughter cell. The bud continues to grow until it separates from the "parent cell", forming a new cell. Under high stress conditions haploid cells will generally die, however under the same conditions diploid cells can undergo sporulation, entering sexual reproduction (meiosis) and producing a variety of haploid spores, which can go on to mate (conjugate), reforming the diploid.

As used herein, the term "budding" refers to a type of cell division in fungi (e.g. yeast) and in protozoa in which one of the "daughter cells" develops as a smaller protrusion from the other. Usually the position of the budding cell is defined by polarity in the "parent cell". In some protozoa the budded daughter may lie within the cytoplasm of the other daughter.

As used herein, the term "daughter cell" refers to one of the two or more cells formed in the division of a parent cell.

As used herein, the term "parent cell" and the term "mother cell" refer to the cell giving rise to daughter cells by cell division.

As used herein, the term "inoculation" refers to the act of introducing a microorganism or suspension of microorganisms (e.g. yeast, fungi, bacteria, etc.) into a culture medium. Inoculation is the act or process of introducing something to where it will grow or reproduce.

As used herein, the term "inoculum" and the term "pre-inoculum" refer to cells used in an inoculation, such as cells added to start a culture.

As used herein, the term "growth procedure" refers to the reproduction of living cells applied to yeast cells where the phrase "cell growth" is shorthand for the idea of "growth in cell numbers by means of cell reproduction." During cell reproduction one cell (the "parental cell" or "mother cell") divides to produce "daughter cells".

As used herein, the term "cultivate yeast" and the term "growing yeast" refer to the act of populating and/or propagating yeast.

As used herein, the term "centrifugation" refers to the separating of molecules by size or density using centrifugal forces generated by a spinning rotor that puts an object in rotation around a fixed axis, applying a force perpendicular to the axis. The centrifuge works using the sedimentation principle, where the centripetal acceleration is used to evenly distribute substances of greater and lesser density into different layers of density.

As used herein, the term "concentration" refers to the amount of a substance per defined space. Concentration usually is expressed in terms of mass per unit of volume. To dilute a solution, one must add more solvent, or reduce the amount of solute (e.g., by selective evaporation, spray drying, freeze drying, e.g., concentrated yeast cell wall extract or concentrated modified yeast cell wall extract). By contrast, to concentrate a solution, one must add more solute, or reduce the amount of solvent.

As used herein, the term "layer" refers to a usually horizontal deposit organized in stratum of a material forming an overlying part or segment obtained after separation by centrifugation in relation with the density properties of the material.

As used herein, the term "harvest" refers to the act of collecting or bringing together materials that have been produced (e.g. bringing together materials produced during yeast production).

As used herein, the term "clay" refers to mineral clays, synthetic, organoclays and any mixture(s) thereof.

As used herein, the term "mineral clay" refers to a naturally occurring or synthetic material composed primarily of fine-grained minerals (silicates) that show plasticity through a variable range of water content (which may be a result of water trapped in the structure by polar attraction) and can be hardened when dried and/or fired. Examples of silicates include, but are not limited to, phyllosilicate, bentonite, zeolite, aluminosilicate, montmorillonite, smectite, kaolinite.

As used herein, the term "organoclay" and the term "modified clay" refer to an organically modified phyllosilicate, derived from a naturally occurring clay mineral. By exchanging the original interlayer cations for organocations (typically quaternary alkylammonium ions) or polysaccharides, an organophilic surface is generated, consisting of covalently linked organic moieties. The lamellar structure remains analogous to the parent phyllosilicate.

As used herein, the term "drying" refers to spray drying, freeze drying, air drying, vacuum drying or any other kind of process that reduces or eliminates liquid in a substance.

As used herein, the term "spray drying" refers to a commonly used method of drying a substance containing liquid using hot gas to evaporate the liquid to reduce or eliminate liquid in the substance. In other words the material is dried by way of spraying or atomizing into a draft of heated dry air.

As used herein, the term "freeze-drying" and the term "lyophilization" and the term "cryodesiccation" refer to the removal of a solvent from matter in a frozen state by sublimation. This is accomplished by freezing the material to be dried below its eutectic point and then providing the latent heat of sublimation. Precise control of heat input permits drying from the frozen state without product melt-back. In practical application, the process is accelerated and precisely controlled under reduced pressure conditions.

As used herein, the term "dry free flowing powder" refers to a free flowing dry powder.

As used herein, the term "grinding" refers to reducing particle size by impact, shearing, or attrition.

As used herein, the term "washing" refers to the removal or cleansing (e.g., using any type of solute (e.g. distilled water, buffer, or solvent) or mixture) of impurities or soluble unwanted component of a preparation (e.g., a yeast cell wall extract may be washed to remove non-yeast cell wall components from the sample).

As used herein, the term "enzyme" refers to as a protein or protein-based molecule with a characteristic sequence of amino acids that fold to produce a specific three-dimensional structure which gives the molecule unique properties and that acts as a catalyst or a chemical for specific chemical reactions, converting a specific set of reactants (called substrates) into specific products.

As used herein, the term "peptide," the term "polypeptide" and the term "protein" refer to a primary sequence of amino acids that are joined by covalent "peptide linkages." Generally, a peptide consists of a few amino acids, typically from 2-50 amino acids, and is shorter than a protein. The term "polypeptide" encompasses peptides and proteins. Peptides, polypeptides or proteins can be synthetic, recombinants or naturally occurring. A synthetic peptide is produced by artificial means in vitro (e.g., was not produced in vivo).

As used herein, the term "proteases" refers to any of various enzymes, including the endopeptidases and exopeptidases that catalyze the hydrolytic breakdown of proteins into peptides or amino acids.

As used herein, the term "lysis" refers to the disintegration or rupture of the yeast cell membrane and yeast cell wall resulting in the release of the intracellular components. As used herein, "lysis" occurs as a result of physical/mechanical, enzymatic (including autolysis and hydrolysis) or osmotic mechanisms (including "alcohol shocking" and hydrolysis).

As used herein, the term "autolysis" refers to the breakdown of a part or whole cell or tissue by self-produced enzymes.

As used herein, the term "hydrolysis", refers to the process of splitting a compound into fragments with the addition of water (e.g., that is used to break down polymers into simpler units (e.g. starch into glucose)).

As used herein, "alcohol shocking" refers to an osmotic stress generated by the addition of an alcohol (e.g. ethanol) to growth medium to create a difference between the osmotic pressure of the medium and the osmotic pressure inside cells (e.g., yeast cells) growing in the medium. Alcohol shocking may lead to the lysis of cells (e.g., yeast cells) grown in the medium.

As used herein, the term "osmosis" refers to the diffusion of a solvent (e.g., water) through a semi-permeable membrane, from a solution of low solute concentration (high water potential) to a solution with high solute concentration (low water potential), up a solute concentration gradient. It is a physical process in which a solvent moves, without input of energy, across a semi-permeable membrane (permeable to the solvent, but not the solute) separating two solutions of different concentrations. Net movement of solvent is from the less-concentrated (hypotonic) to the more-concentrated (hypertonic) solution, which tends to reduce the difference in concentrations.

As used herein, the term "osmotic stress" and the term "osmotic shock" refer to a sudden change in the solute concentration around a cell, causing a rapid change in the movement of water across its cell membrane. Under conditions of high concentrations of either salts, substrates or any solute in the supernatant water is drawn out of the cells through osmosis. This also inhibits the transport of substrates and cofactors into the cell thus "shocking" the cell. Alternatively, at low concentrations of solutes, water enters the cell in large amounts, causing it to swell and either burst or undergo apoptosis.

As used herein, the term "sample" is used in a broad sense including a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples.

As used herein, the term "complex" refers to an entity formed by association between two or more separate entities (e.g., association between two or more entities wherein the entities are the same or different (e.g., same or different chemical species). The association may be via a covalent bond or a non-covalent bond (e.g., via van der Waals, electrostatic, charge interaction, hydrophobic interaction, dipole interaction, and/or hydrogen bonding forces (e.g., urethane linkages, amide linkages, ester linkages, and combination thereof)).

DETAILED DESCRIPTION OF THE INVENTION

The present invention provides novel yeast cells comprising a cell wall structure that has been modified (e.g., clay and/or clay components are interlaced into the yeast cell wall and/or the glucan:mannan ratio has been altered), methods of producing the same, compositions comprising and/or derived from the same, and methods of using the same (e.g., to sequester bacteria and mycotoxins).

In some embodiments, the present invention provides a yeast cell wall extract (e.g., an isolated, purified, modified and/or concentrated cell wall extract) comprising clay and/or clay component(s) interlaced into the cell wall (e.g., due to cultivation of the yeast cell in the presence of a clay) and/or yeast cell wall extract comprising altered glucan:mannan structure. In some embodiments, the clay interlaced yeast cell wall extract comprising clay and/or clay component interlaced into the yeast cell wall and/or yeast cell wall extract comprising altered glucan:mannan structure is admixed or otherwise added to feedstuffs, organic matter (e.g., bedding), and/or water thereby sequestering mycotoxins (e.g., while in the gastrointestinal tract of the animal or during filtration), and negating or reducing the negative effects of mycotoxins. Thus, in some embodiments, the present invention provides methods that significantly improve the adsorptive/sequestering properties of yeast cell wall-based material toward mycotoxins (e.g., that significantly adsorb and/or sequester and/or limit the bioavailability of a variety of mycotoxins (e.g., not adsorbed to and/or not sequestered using clay alone, yeast cell wall extract alone, a combination of yeast cell wall extract to which a clay is later added on a dry blend basis; and/or a chemical grafting of polysaccharide materials on top of clay based products) in the digestive tract of an animal).

In some embodiments, the present invention provides a novel preparation of yeast cells grown in the presence of one or more clays. In some embodiments, clay interlaced yeast cell walls are extracted from the clay interlaced yeast cells grown in the presence of one or more clays. In some embodiments, the clay interlaced yeast cell wall extract is purified and/or concentrated. As described herein, the present invention is not limited to any particular yeast cell strain or to any particular clay. In some embodiments, the clay source is a standard commercial grade clay source (e.g., selected for exhibiting in vitro, in vivo, and/or ex vivo properties toward mycotoxins, or a clay source selected because it does not exhibit in vitro, in vivo, and/or ex vivo properties toward mycotoxins). Compositions and methods of the present invention can be utilized for adsorbing and/or sequestering of mycotoxins in a variety of subjects. Indeed, the present invention is not limited by the type of subject that benefits from the compositions and methods described herein. The present invention can benefit all animals, however, exemplary subjects include, but are not limited to, humans, avian, bovine, porcine, equine, ovine, caprine, canine, feline, piscine, camelid, rodent species as well as fish and shellfish subjects. In some embodiments, when admixed with organic matter (e.g., including bedding and feedstuffs), and/or water, and/or fed directly to a subject, compositions of the present invention decrease the absorption or uptake of mycotoxins by the subject, thereby alleviating reduced performance, health and/or reducing the incidence mycotoxin-associated diseases and pathological responses in the subject.

In some embodiments, the present invention provides a method for making and/or generating yeast cells comprising clay and/or clay component(s) interlaced into the yeast cell wall, and/or comprising an altered glucan:mannan structure. For example, in some embodiments, the present invention provides a yeast cell generated and/or cultivated in the presence of a clay wherein the yeast cell wall comprises a glucan:mannan ratio that is greater than (e.g., 2.5% greater, 5% greater, 10% greater, 15%, 20% greater, 25% greater, 30% greater, 40% greater, 50% greater or more) the glucan:mannan ratio of yeast cells generated/cultivated in the absence of a clay (See, e.g., Example 2). In some embodiments, the present invention provides a yeast cell wall extract obtained from (e.g., isolated, purified and/or concentrated from) a viable yeast cell generated and/or cultivated in the presence of a clay wherein the yeast cell wall comprises a glucan:mannan ratio that is greater (e.g., 2.5% greater, 5% greater, 10% greater, 15%, 20% greater, 25% greater, 30% greater, 40% greater, 50% greater or more) than the glucan:mannan ratio of yeast cells generated/cultivated in the absence of a clay (See, e.g., Example 2).

Thus, the present invention provides novel, clay interlaced yeast cell wall extract from yeast cultivated in the presence of a clay, and methods of generating the same. In some embodiments, a method of generating yeast cells comprises cultivating yeast cells including, but not limited to, *Saccharomyces*, *Candida*, *Kluyveromyces*, and *Torulaspora* species in the presence of one or more clays in order to alter or otherwise modify the yeast cell wall (e.g., in order to enhance the ability of the yeast cell wall to adsorb and/or sequester mycotoxins (e.g., due to the yeast cell wall interlaced with clay and/or clay component(s) and/or comprising an altered glucan:mannan structure)). In some embodiments, the present invention provides the blending of one or more clay based materials including, but not limited to, silicates (e.g., group of tectosilicates (e.g., zeolites, quartz, feldspars); phyllosilicates (e.g., kaolinite, halloysite, dicktite, nacrit, chysotile, antigorite, lizardite, talc), pyrophyllites, smectites (e.g., montmorillonite, beidellite, nontronite; vermiculites, micasantigorite, muscovite, illite, phengite, biotite); sepiolite, palygorskite, attapulgite), and/or a hydrated aluminum silicate (e.g., montmorillonites, bentonite)) to a yeast cell culture medium (e.g., as described in Examples 1, 5, and 6). The present invention provides that the viable yeast cells incorporate the clay and/or clay components into the yeast cell wall structure (e.g., as shown in FIGS. 1A and 1B and FIG. 2). In some embodiments, the one or more clays blended into a yeast cell culture medium are present at a concentration of about 0.075%, 0.1%, 0.125%, 0.25%, 0.5%, 1%, 2%, 4%, 5%, 6%, 7%, 8%, 9%, 10%, 12%, 15%, or more of the total growth medium. In some embodiments, the amount of one or more clays blended into a yeast cell culture medium does not exceed 2% of the final content of a reactor in which the yeast cells are grown. In some embodiments, an amount of clay added to yeast cell culture medium is chosen that does not lead to swelling of the yeast cell culture medium (e.g., is about 2.0% or less). In some embodiments, the amount of clay added to yeast cell culture medium is chosen that produces a yeast cell wall extract harvested from the yeast that comprises an amount of clay that has regulatory approval for use as a feed additive in non-medicated animal feed (e.g., does not to exceed 2% in total ration). In some embodiments, a food-grade anti-foaming agent or defoamer is added to the cell culture medium, (e.g., including but not limited to, nonsilicone molecular defoamers, oil based defoamers (e.g., mineral oil, vegetable oil, white oil, or other oil that is insoluble in the foaming medium) or silicone compound based defoamers (e.g., delivered as an oil or water based emulsion)). In some embodiments, waxes (e.g., ethylene bis stearamide (EBS), paraffinic waxes, ester waxes or fatty alcohol waxes) and/or hydrophobic silica are added to improve emulsification and spreading in the foaming medium.

Experiments conducted during development of embodiments of the invention identified a number of factors as important for growth of yeast cells in the presence of one or more clays. For example, in some embodiments, it is preferred to maintain the (w/v) relationship (e.g., corresponding to grams/cubic centimeter (g/cc)) between the clay support material and the water at or below 3% (e.g., to avoid reaching a solid or semi-solid state (e.g., due to water adsorption and retentiveness of the clay material)). Thus, water sorption of the water-swellable hydrated aluminum silicate is a limiting factor impacting the ratio of clay support material to water in the formulation of a culture medium of the present invention. In some embodiments, culture media and bottles used are sterilized, and inoculation with microorganisms is effected in accordance with standard procedures. For example, in some embodiments, a pre-inoculum is prepared with active dry yeast in a bottle of sterile deionized water and incubated at about 25-30° C. (e.g., 28° C.) for a set period of time (e.g., 20 min). In some embodiments, inoculation of the pre-inoculum is aseptically performed (e.g., at a temperature of about 30° C.). In some embodiments, pH and glucose levels are monitored and maintained. In some embodiments, agitation of the culture is increased incrementally (e.g., from 100 to 500 rpm) during growth. In some embodiments, one or more clays are added aseptically to the culture during growth (e.g., when less than half, about half, or more than half of the culture nutrients are consumed).

In some embodiments, as the amount of clay blended into the yeast cell culture medium increases (e.g., in an amount dependent upon the type of clay or clays used) the swelling properties of the clay material inhibits yeast cell growth.

In some embodiments, growing yeast in clay-blended yeast cell culture medium provides conditions which stress the growing yeast. Although the present invention is not limited to any particular mechanism of action, and an understanding of the mechanism of action is not necessary to practice the present invention, in some embodiments, the stress applied to the yeast by the clay-blended cell-culture medium causes yeast to produce more glucan, resulting in increased ratios of glucan:mannan.

In some embodiments, the present invention provides that yeast cells cultivated in the presence of one or more clays not only interlaces the clay and/or a component of the clay into the yeast cell wall, but also display an altered cell wall composition (e.g., characterized by altered ratios of glucan:mannan, total protein content, and/or remnant amounts). For example, the present invention provides yeast cells comprising a glucan:mannan ratio that is greater (e.g., 2.5% greater, 5% greater, 10% greater, 15%, 20% greater, 25% greater, 30% greater, 40% greater, 50% greater or more) than the glucan:mannan ratio of the yeast cells cultivated in the absence of clay (See, e.g., Example 2). The present invention also provides yeast cells and yeast cell wall extracts comprising an enhanced total protein content (e.g., 100%, 200%, 300%, 400%, 500% or more enhance protein content) compared to the total protein content of yeast cells and/or yeast cell wall extracts generated in the absence of a clay (See, e.g., Example 2).

In some embodiments, the present invention provides yeast cell wall extracts comprising clay and/or clay component(s) interlaced into the yeast cell wall and/or comprising an altered glucan:mannan ratio of the structure, that provides superior mycotoxin sequestration properties than conventional compositions. The present invention is not limited by any particular method of generating a yeast cell wall extract from yeast cultivated in the presence of one or more clays. Indeed, a variety of procedures may be utilized to generate yeast cell wall extracts including, but not limited to, use of glass beads and a bead beater, enzymatic (e.g., protease (e.g., papain)) treatment, mechanical lysis, autolysis and hydrolysis, and other methods known in the art (See, e.g., Peppler, H. J. 1979. Production of yeasts and yeast products. Page 157 in: Microbial Technology & Microbial Processes, Vol. 1 (2d Ed.), Academic Press). Following lysis and extraction, clay and/or clay component interlaced/integrated yeast cell wall is washed to remove intracellular components and to purify and concentrate the extract. The resulting extract may be dried by any of a number of methods common in the art including, but not limited, freeze-drying and/or spray-drying (e.g., to form a hygroscopic water-insoluble powder).

Accordingly, the invention provides, in some embodiments, yeast cell wall extract comprising clay and/or clay component interlaced directly into the yeast cell wall. In some embodiments, a composition comprising a yeast cell wall extract of the invention comprising clay and/or clay components integrated directly into the yeast cell wall comprises less than about 0.5% clay, 0.5-1%, 1-2%, 2-5%, 5-10%, 10-15%, 15-20%, 20-30%, 30-40%, 40-50%, 50-60%, 60-70%, 70% or more clay and/or clay component as part of a yeast cell wall extract (on a w/w % basis). In some embodiments, increasing the amount of clay in a culture medium increases the amount of clay and/or clay component content of a yeast cell wall extract.

In some embodiments, clay that is added to yeast cell growth medium that is not incorporated into a yeast cell is collected and utilized in a subsequent yeast cell growth procedure (e.g., the unincorporated clay material is recycled). For example, recycling of clay material is facilitated by the sedimentation properties of the clay compared to yeast. Indeed, experiments conducted during development of embodiments of the invention have produced two recoverable layers, (i) a bottom layer containing clay material only (at 99%); and (ii) a top layer containing a clay fraction incorporated into yeast. Thus, although a mechanism is not necessary to practice the present invention and the present invention is not limited to any particular mechanism of action, in some embodiments, the present invention provides a direct inclusion of clay particles into and/or onto the yeast cell wall (e.g., that survives yeast cell wall extract preparation processes (e.g., via direct interlacing of clay or clay component into the glucan polymer chains of the yeast cell wall)). In other embodiments, a clay fraction traps a yeast cell during culture and upon budding, together with daughter cells, the yeast cells are encaged in a clay comprising macrostructure before the yeast is lysed and its intracellular components removed by washing. In some embodiments, glucan chains grow in between the lamellar structure of the clay.

In some embodiments, a yeast cell or yeast cell wall component (e.g., a yeast cell wall extract generated and isolated as described herein (e.g., comprising clay or clay component interlaced into the yeast cell wall and/or comprising an altered glucan and/or mannan structure)) is combined with one or more other agents including, but not limited to, an enzyme (e.g., esterase, epoxidase), a bacteria, a yeast or yeast component, clay, etc. (e.g., prior to admixing with feeds, incorporating into pelleted feeds, and/or feeding to animals)).

In some embodiments, the present invention utilizes yeast cells comprising altered yeast cell wall structure (e.g., clay and/or clay component interlaced into the yeast cell walls and/or cell walls comprising altered glucan and/or mannan structure), compositions comprising the same, and/or compositions derived from the same, that are utilized with one or more methods and/or materials described herein for use in compositions and/or methods for the reduction, removal and/or elimination of mycotoxins (e.g., physical, mixing, chemical, microbiological methods described herein (e.g., to adsorb and/or sequester bacteria and toxins)). For example, in some embodiments, a yeast cell or yeast cell wall component (e.g., a yeast cell wall extract produced as described herein (e.g., comprising clay or clay component(s) interlaced into the yeast cell wall and/or comprising an altered glucan and/or mannan structure)) is utilized with one or more physical, mixing, chemical, or microbiological methods described herein to sequester mycotoxins.

The present invention is not limited by the type of mycotoxin sequestered. Indeed, compositions of the present invention (e.g., clay interlaced yeast cell wall extracts) can be utilized to adsorb and/or sequester a variety of mycotoxins including, but not limited to, acetoxyscirpenediol, acetyldeoxynivalenol, acetylnivalenol, acetylneosolaniol, acetyl T-2 toxin, extended to all aflatoxins, aflatoxin B1, B2, G1 and G2, aflatrem, altenuic acid, alternariol, austdiol, austamide, austocystin, avenacein +1, beauvericin +2, bentenolide, brevianamide, butenolide, calonectrin, chaetoglobosin, chaetocin, chaetomin, citrinin, citreoviridin, cochliodinol, cytochalasins, cyclopiazonic acid, deacetylcalonectrin, deactylneosolaniol, deoxynivalenol diacetate, deoxynivalenol monoacetate, diacetoxyscirpenol, destruxin B, emestrin, enniatins, extended to all ergot alkaloids toxins and endophytes such as ergine, ergocornine, ergocristine, ergocryptine, ergometrine, ergonine, ergosine, ergotamine, ergovaline, lysergol, lysergic acid, and related epimers, fructigenin +1, fumagilin, fumonisins, fumonisins A1, A2, B1 and B2 and B3, fusarenon-X, fusarochromanone, fusaric acid, fusarin, gliotoxin, HT-2 toxin, hyalodendrin, ipomeanine, islanditoxin, isofumigaclavines A and B, lateritin +1, leptosin, lycomarasmin +1, malformin, maltoryzine, moniliformin, monoacetoxyscirpenol, mycophenolic acid, neosolaniol, nivalenol, NT-1 toxin, NT-2 toxin, extended to all ochratoxins, oosporein, oxalic acid, paspalitrem A and B, patulin, penicillic acid, penitrem, phomopsins, PR-toxin, roridin E, roquefortine A and B, rubratoxin, rubroskyrin, rubrosulphin, rugulosin, sambucynin +1, satratoxins, F, G, H, scirpentriol, sirodesmin, slaframine, sporidesmin, sterigmatocystin, swainsonine, T-1 toxin, T-2 toxin, tenuazoic acid, triacetoxyscirpendiol extended to all trichothecenes, trichodermin, trichothecin, trichoverrins, trichoverrols, tryptoquivalene, verrucarin, verruculogen, verticillins, viopurpurin, viomellein, viriditoxin, wortmannin, xanthocillin, yavanicin+1, zearalenols, zearalanones, zearalenone, α, β, zearalanone, α, β, zeranol and subfamilies and/or derivatives of the same, and/or conjugates. In some embodiments, compositions and methods of the invention are utilized to adsorb and/or sequester aflatoxins, zearalenone, ochratoxins, trichothecene, fumonisin, patulin, and/or endophyte related ergot and possible conjugates and metabolites of the aforementioned mycotoxins. Experiments conducted during development of the present invention demonstrate the benefit(s) of using the present invention compared to historical or conventional methods. For example, as described herein, a drawback of using a composition comprising only (1) a clay, (2) a composition comprising only a yeast cell wall extract, as well as (3) a composition comprising a yeast cell wall extract to which a clay has been added, is that such compositions and methods of using the same are less effective means than the present invention for reducing the negative effects of mycotoxins and have more drawbacks. However, clay interlaced yeast cell wall extracts of the present invention (e.g., comprising clay and/or clay component interlaced into the yeast cell wall, and/or comprising an altered glucan and/or mannan structure) display the unexpected ability to sequester a variety of mycotoxins, and also display a strikingly enhanced ability to adsorb mycotoxins compared to conventional compositions (e.g., a composition comprising only clay(s), a composition comprising only a yeast cell wall extract, as well as a composition comprising a yeast cell wall extract to which clay(s) has been added, See Examples 2-3). Thus, the present invention provides compositions and methods that display unexpected and superior sequestration and/or adsorption properties with respect to a variety of mycotoxins not found in conventional compositions and methods. Thus, the present invention provides clay interlaced yeast cell wall-based materials and methods of making and using the same to provide an efficient method to sequester mycotoxins in the digestive tract of animals and humans (e.g., via adsorbing mycotoxins present in feedstuffs, other organic matter and/or water) while also providing lower or no adsorption of beneficial nutrients and lesser or no negative effects on the environment.

In some embodiments, a preferred physical form of the invention is a dry free-flowing powder suitable for direct inclusion into feedstuffs, other organic matter (e.g., bedding) or as a direct supplement to an animal.

Compositions of the invention can be added to any organic matter (e.g., bedding, feedstuff for animals, feedstuff for humans) and/or water (e.g., water used for animal and/or human consumption, environmental water (e.g., ponds, lakes, reservoirs, fish tanks, etc.)) to remove mycotoxins from the matter. When incorporated directly into animal feedstuffs, a composition of the invention is added in amounts ranging from about 0.0125% to about 0.4% by weight of feed. When incorporated into other organic matter (e.g., animal bedding), a composition of the invention is added in amounts ranging from about 0.0125% to about 99.9%. When incorporated into a liquid (e.g., water (e.g., for filtration)), a composition of the invention is added in amounts ranging from about 0.0125% to about 100%. In some embodiments, a composition of the invention is added to feedstuffs in amounts from about 0.025% to about 0.2% by weight of feedstuff. Alternatively, compositions of the invention are directly fed to animals as a supplement (e.g., in an amount ranging from about 2.5 to about 20 grams per animal per day). One of ordinary skill in the art immediately appreciates the amount to be fed varies depending upon animal species, size, the type of feedstuff to which a composition of the invention is added, bedding material, water source, etc.

Compositions of the invention can be fed to any animal and humans. When admixed with feedstuffs or used as a feed supplement, compositions of the invention decrease mycotoxin bioavailability, absorption or uptake of mycotoxins by the animal, improve performance and/or health and reduce incidence of disease. In some embodiments, when, compositions of the invention are added to organic material that animals and humans come into contact with (e.g. bedding), compositions of the invention decrease mycotoxin bioavailability (e.g., decrease absorption and/or uptake of mycotoxins by the animal) thereby improving performance and health and reducing incidence of disease. In some embodiments, compositions of the invention are added to water that is intended for use by animals or humans (e.g., for consumption or other purpose), thereby decreasing mycotoxin bioavailability (e.g., decrease absorption and/or uptake of mycotoxins by an animal or human subject) and improving performance and health and reducing incidence of disease (e.g., compositions of the invention decrease bioavailability, absorption or uptake of mycotoxins). In some embodiments, a composition of the invention is added to water used for human consumption (e.g., water used for manufacture of juice, wine, water bottles, coffee, tea, milk or other type of consumed liquid). In some embodiments, a composition of the invention is added to environmental water (e.g., ponds, lakes, reservoirs, rivers, streams, irrigation channels, tanks used to house fish or other type of aquatic species, etc.). Thus, in some embodiments, a composition of the invention (e.g., yeast cell wall extract comprising clay or clay component integrated into the cell wall) is utilized in the filtration of liquids (e.g., consumable liquids (e.g., water used in beverage production, beverages)). For example, in some embodiments, a composition of the invention is utilized as or in a filter, wherein a liquid (e.g., consumable liquid (e.g., orange juice, apple juice, prune juice, grapefruit juice, cranberry juice, or other type of juice, beer, wine, distilled liquid, etc.)) is processed through a filter comprising a composition of the invention, wherein the composition removes one or more types of mycotoxins from the liquid.

As described in Examples 1-4, cultivation of yeast in the presence of clay provides a dramatic increase in the yeast cell wall adsorption of mycotoxins (e.g., from 6.917% when the yeast is not cultivated with clay, and reaching 73.553% and 79.337% when 1.0 and 2.0% of clay are respectively included to the medium without the specific extraction of the glucan of the inner yeast cell wall layer (See, e.g., Example 2)). Moreover, the ratio of glucan:mannan increases from 1.066 to 1.366 with the addition of clay. Despite a decrease of mannan, the concentration of the proteins of the cell wall increased. Also, the remnant fraction (e.g., representing losses of glucans, mannan, proteins, clay, N-acetylglucosamine and/or chitin present in the yeast cell wall during the extraction process) increased in the presence and surface area of clay. Although a mechanism is not necessary to practice the invention and the invention is not limited to any particular mechanism of action, in some embodiments, the increase is due to the enhancement of chitin fraction involved in compensatory mechanisms of the yeast due to changes of the environment and conditions of growth. Moreover, compositions of the present invention (comprising yeast cell wall extract from altered yeast cells (e.g., yeast cells comprising clay and/or clay component interlaced into the yeast cell walls and/or cell walls comprising altered glucan and/or mannan structure)) provided a significant and unexpected ability to adsorb and/or sequester mycotoxins (e.g., zearalenone (e.g., displaying a 79.33% efficacy compared to only a 44.7% efficacy for a conventional composition comprising a combination of yeast cell wall extract to which a clay is later added on a dry blend basis, See Examples 1-4)).

The use of an alternative method to extract clay interlaced yeast cell wall of clay interlaced yeast cells using a protease cut was investigated (See Example 3). The specific extraction of the inner layer (glucan) of clay interlaced yeast cell wall generated an increase of the sequestering and adsorption properties of the clay interlaced yeast cell wall for mycotoxins (e.g., zearalenone). Moreover, cultivating yeast cells in a cell culture medium comprising clay at 1.0% and 2.0% enhanced significantly the sequestering and adsorption activity of clay interlaced yeast cell wall with mycotoxins, (e.g. zearalenone). For example, a conventional composition comprising a combination of yeast cell wall extract to which a clay is later added on a dry blend basis accounted for a 44.7% efficacy rate for sequestering mycotoxins, compared to a 85.89% efficacy rate for sequestering mycotoxins obtained with a composition of the present invention and an increase of aflatoxin B1 adsorption from 2.65 up to 53.70% (See, e.g., Example 3).

In some embodiments, the present invention provides methods for producing yeast cells comprising a clay-interlaced yeast cell wall. In some embodiments, yeast cells comprising a clay-interlaced yeast cell wall are produced on a variety of scales (e.g. test scale, batch-scale, pilot-scale, pre-production-scale, production-scale, commercial-scale, industrial scale). In some embodiments, yeast are grown in a fermenter. A fermenter may be of any suitable size (e.g. 5 liter . . . 10 liter . . . 25 liter . . . 50 liter . . . 100 . . . 500 liter . . . 1K liter . . . 5K liter . . . 10K liter . . . 50K liter . . . 100K liter . . . 500K liter . . . 1 million liter, etc.) to produce the desired scale of yeast for use with the present invention (e.g. test-scale, pilot scale, industrial-scale, etc.). In some embodiments, media for growing yeast can be of any suitable composition for growing yeast in accordance with the present invention. Suitable nutrients are sources of carbon, nitrogen, phosphorus, magnesium, sulphur, potassium and trace elements. In some embodiments, nutrients are added to the culture in concentrations (% w/w of the source compound) within the ranges (percentages by weight): Carbon source 0.01-20% (e.g. 0.05-10%), Nitrogen source 0.001-10% (e.g. 0.001-3%), Phosphorus source 0.001-5% (e.g. 0.01-0.5%), Magnesium source 0.001-0.2% (e.g. 0.001-0.2%), Sulphur source 0.01-0.25% (e.g. 0.01-0.25%), Potassium source 0.001-05% (e.g. 0.01-0.25%), Organic nitrogen source 0.001-5% (e.g. 0.01-5%), and trace elements are added in excess. In some embodiments, yeast culture media comprises water, carbon source (e.g. sugar, glucose, dextrose, sugar cane, molasses, etc.), suitable nitrogen source (e.g. ammonia, urea, etc.), amino acid source (e.g. peptone, etc.), salts (e.g. sodium chloride, calcium hipochloride, magnesium chloride, magnesium sulphate, zinc sulphate, etc.), and source of clay or clay component (e.g. zeolite, bentonite, aluminosilicate, montmorillonite, smectite, kaolinite, organoclay, mixtures thereof, etc.). In some embodiments, yeast culture media components may be present in any suitable amounts for yeast cell growth (See e.g. Example 5). In some embodiments, the presence of clay in yeast culture media presents unanticipated complications to standard yeast growing protocols. In some embodiments, the presence of clay in culture media results in unusually large amounts of foaming in the fermentor. In some embodiments, the present invention provides antifoaming agents in the cell culture medium (e.g. nonsilicone molecular defoamers, oil based defoamers (e.g. mineral oil, vegetable oil, white oil, etc.), powder defoamers (e.g. silica), water based defoamers, silicone based defoamers, polyethylene glycol polypropylene glycol copolymers, alkyl polyacrylates, etc.). In some embodiments, antifoaming agents are required for increasing the scale of the present invention. In some embodiments, use of an antifoaming agent is associated with an enhanced ability to scale up production of a composition of the invention

EXPERIMENTAL

The following examples are provided in order to demonstrate and further illustrate certain preferred embodiments and aspects of the present invention and are not to be construed as limiting the scope thereof.

Example 1

Materials and Methods

Yeast Culture.

The following protocol was used for each Bioflow fermenter (BioFlow III, New Brunswick Scientific Co., Inc., Edison, N.J., U.S.A.) to grow the yeast *Sacchromyces cerevisiae* (active dry yeast (ADY) from Fermin, Alltech Inc., Batch #689, Yeast count: $2.38 \times 10^{10}$ cells/gram, Viability: 92.6%). The yeast inoculum was prepared by transferring 28 g of fresh ADY Fermin to a pre-warmed bottle of 250 mL sterile deionized water. Then, the solution was incubated at 30° C. (in water bath) for 20 min and swirled several times. The BioFlow media was composed of 66 g of yeast extract, 10 g of peptone, 4 g of dextrose, 4 g of yeast nitrogen base and 1750 mL of deionized water. A control batch was produced by growing yeast alone, which required an additional 250 mL of deionized water to the reactor volume. Three batches containing yeast and bentonite K10 (Fluka) were produced by adding 8, 16, and 32 g to the reactor. The Bioflow reactor media was warmed up at 30° C. and air was injected at 1 L/min flow rate during 10 min prior inoculation. Agitation was set at 300 rpm and the media monitored and maintained at a minimum of pH 5.0 during the entire growth. An anti-foaming agent was added (Antifoam AES, 1:10, as needed). Ammonium phosphate dibasic (DAP) was then injected aseptically (4 g in 10 mL at pH 4.0). The previously re-suspended yeast was added to the fermentor. The glucose level was tested during growth with diabetic stripes (OneTouch, UltraMini, LifeScan, Inc., Milpitas, Calif., U.S.A.) and supplemental glucose was added when glucose level fell below 0.8 mg/mL. The agitation was progressively increased to 500 rpm over 2 h of incubation as well as the air flow (up to 4 L/min over 3 h). When half of the supplemental glucose substrate was consumed, additional bentonite was added (8, 16, 32 g in 250 mL deionized water) to the reactor for a final concentration of 0.5%; 1.0%; and 2.0%, respectively, of clay in the final media.

Yeast cultures were harvested when all sugar had been utilized. The content of the BioFlow was collected into sterile bottles and centrifuged at 4000 g for 20 min. The supernatant was removed and the pellet was washed with 0.125% NaCl in H2O. The pellet was separated into 2 fractions by the distinct formation of 2 layers after centrifugation: (i) a clay containing layer and (ii) a yeast and clay containing layer. Yeast were then washed three times with 0.125% NaCl solution.

Clay Interlaced Yeast Cell Wall Extraction Method.

Two separate methods were used for the isolation of yeast cell wall fractions from yeast produced as described above.

In a first method, a 'micro-method' was used employing glass beads and a minibead beater (Bead-Beater, Model #1107900, Biospec Products, Inc., Hamilton Beach/Proctor-Silex, Inc., Southern Pines, N.C., U.S.A.). The pellet was resuspended with two volume of 10 mM Tris-Cl, pH 7.4 with phenylmethylsulfonofluoride (PMSF) and beat with glass beads (50:50, yeast slurry:beads) in a total volume of 5 mL for 30 sec with 1 min interval rest, all the while on ice. The beating was repeated 10 times or until 95% of the cells were disrupted. The beads were re-collected and washed. The fractions were pooled and centrifuged at 4000 g for 20 min. The pellets were then collected, freeze-dried and ground.

In a second method, the yeast pellet was resuspended with sterile deionized water to a concentration of 13 to 15% of dry matter. The yeast slurry was stirred at 60° C. The pH was adjusted using 10% NaOH to 8.0 before adding enzyme at 0.3 mL/L. The temperature and stirring conditions were maintained over 8 h. The pH was monitored and adjusted every 15 min (using the 10% NaOH) for the first two hours, and then the pH was monitored and adjusted every hour for the next six hours. The slurry was transferred to sterile centrifuge bottles and centrifuged at 4000 g for 20 min. The supernatant was discarded and the pellet washed with three volume of cold sterile water, and then centrifuged again at 4000 g for 20 min. The washing step was repeated two times before the pellet was frozen, freeze dried and ground.

Example 2

Characterization of Yeast Cell Wall Extracts Isolated Utilizing Glass Beads and a Minibead Beater from Yeast Cells Cultivated in the Absence and Presence of Clay Yeast cells were disrupted after re-suspension of the cells in Tris-HCl buffer, pH 7.4 with PMSF using a micro-method using a bead-beater and glass beads as described (See Example 1). Yeast cell wall lysates were then analyzed in order to characterize the yeast cell walls and their ability to adsorb mycotoxins (expressed as a percent of efficacy compared to total mycotoxins present) under physiological pH conditions for each individual mycotoxin considered. The overall adsorbing/binding activity was evaluated kinetically. Test samples comprised a minimum of 5 levels up to 10 levels of mycotoxin concentrations tested with the different yeast cell wall preparations used at a concentration between 0.25 and 4 g/L dispersed in an aqueous medium with a fixed value of pH 4 representative of digestive conditions of pH in the animal tract. Adsorption evaluation was calculated using a High Performance Liquid Chromatography (abbrev. HPLC) coupled to fluorometric and diode-array detectors (e.g., to detect amounts of mycotoxin and mycotoxin adsorbed/sequestered).

Data is shown in FIG. 3. Yeast cell wall extracts obtained from yeast cells cultured in the presence of clay (clay interlaced yeast cells) display a significant, unexpected, ability to sequester and to adsorb zearalenone (e.g., displaying a 79.33% efficacy for yeast cell walls extracted from yeast cells cultivated in the presence of 2% clay compared to only 6.91% efficacy of yeast cell walls extracted from yeast cells cultivated in the absence of clay. The 79.33 efficacy rate for yeast cell wall compositions extracted from yeast cells cultivated in the presence of 2% clay was also significantly higher than previously documented efficacy rates of only 44.7% for a conventional composition comprising a combination of yeast cell wall extract to which a clay is later added on a dry blend basis. The level of inclusion of the sequestrants product for AFB1 and ZEA were respectively of 0.1 and 0.4% in the reaction medium that was maintained at a constant pH of 4.0. The assay was performed under orbital agitation during 90 min at 37° C. and the amount of bound toxin evaluated using HPLC equipped with a fluorescent detector.

Additionally, yeast grown/cultivated in the presence of clay displayed significant alteration in cell wall component/structure. For example, as the amount of clay was increased, the ratio of mannan:glucan increases (e.g., as clay increases from none, 0.5%, 1.0% to 2.0%, the mannan:glucan ratio increases from 1.01 to 1.2, 1.35 and 1.45, respectively. The total amount of protein also increased with increasing amounts of clay added to the cell culture medium.

Example 3

Characterization of Yeast Cell Wall Extracts Isolated Utilizing Protease Cutting from Yeast Cells Grown/Cultivated in the Absence and Presence of Clay Yeast cells were treated with a protease as described in Example 1. Yeast cell wall lysates were then analyzed in order to characterize the yeast cell walls and their ability to adsorb mycotoxins (expressed as a percent of efficacy compared to total mycotoxins present) under physiological pH conditions for each individual mycotoxin considered. The overall adsorbing activity was evaluated kinetically. Tests samples comprised a minimum of 5 levels up to 10 levels of mycotoxin concentrations tested with the different yeast cell wall preparations used at a concentration between 0.25 and 4 g/L dispersed in an aqueous medium with a fixed value of pH 4) representative of digestive conditions of pH in the animal tract. Adsorption evaluation was calculated using a HPLC coupled to fluorometric and diode-array detectors (e.g., to detect amounts of mycotoxin and mycotoxin adsorbed/sequestered).

Data is shown in FIG. 4. Clay interlaced yeast cell wall extracts obtained from yeast cells cultured in the presence of clay displayed a significant, unexpected, ability to sequester and/or adsorb zearalenone and aflotoxin B1. For example, yeast cell wall extracts obtained from yeast grown in the presence of 2.0% clay displayed an 85.89% efficacy for zearalenone whereas yeast cell wall extracts from yeast cultivated in the absence of clay display only a 69% adsorption efficacy rate. Clay interlaced yeast cell wall extracts obtained from yeast grown in the presence of 2.0% clay displayed a 53.7% efficacy for aflatoxin B1 whereas yeast cell wall extracts from yeast cultivated in the absence of clay display only a 2.65% adsorption efficacy rate. Additionally, clay interlaced yeast grown/cultivated in the presence of clay displayed significant alteration in cell wall component/structure. The level of inclusion of the sequestrants product for AFB1 and ZEA were respectively of 0.1 and 0.4% in the reaction medium that was maintained at a constant pH of 4.0. The assay was performed under orbital agitation during 90 min at 37° C. and the amount of bound toxin evaluated using HPLC equipped with a fluorescent detector.

The method of Example 1 was used with alternate sources of yeast to evaluate the influence of a smectite clay (American Colloid Company, Arlighton Height, Ill., USA) added at 1.0% in the growing media on the composition of the clay interlaced yeast cell wall material. Three yeast types were investigated belonging to *Saccharomyces cerevisiae*, ADY Fermin (08-032/460-89), a baker's yeast from Levapan (Batch #7169281, Levapan S.A., Bogota, Columbia) and an active dry yeast from DCL (lot #1390, DCL Yeast Ltd., Alloa, Great Britain).

Variation between the clay interlaced yeast cell wall were observed with levels of 19.9, 17.0, and 10.3% of glucan; 10.6, 10.4, and 8.4% of mannan; and 1.5, 1.4, 0.9% of chitin (N-acetyl-glucosamine) present in the yeast cell wall (and expressed by reference to the total cell) for ADY Fermin, Levapan, DCL clay interlaced yeast cell walls prior hydrolysis.

The sequestration efficacy of the produced material exhibited also differences according to the yeast cell type selected (See, e.g. FIG. 9). The variations observed in terms of efficacy were also related to the type of mycotoxin considered.

Example 4

Electron Microscopy Imaging of Yeast Cell Wall Extracts from Yeast Cells Grown/Cultivated in the Absence and Presence of Clay Experiments were conducted during development of embodiments of the invention in order to characterize and observe several yeast samples (See, e.g., FIG. 2). The samples were prepared by the filtration of a rehydrated solution of yeast in 2.5% glutaraldehyde (GTA) in 0.85% NaCl solution. The solution was then filtered through a nylon nucleopore 13 mm diam., 0.1 μm pore size pre-wetted with 0.85% NaCl. The filter was then transferred to a Petri dish and covered with drops of GTA/cacodylate (Cac) fixative at room temperature during 90 min. The filters were then rinsed with 0.1 M Na Cac pH 7.2. The secondary fixation was achieved by placing the filters in a tube during 60 min with 100 μL of 2% osmium tetroxide in 0.1 M Na Cac pH 7.2. The samples were then rinsed with 0.1 M Na Cac pH 7.2 and 3 times with deionized water. The dehydration of the sample was achieved by ethanol series (25% to 100%). Then, the samples were freeze-dried, mounted on a stub prepared with a carbon tape for conductivity purpose, and coated with Au/P alloy. The observations were made at 3.0 keV on an S-4300 FESEM (Hitachi, Japan). To remove any unspecific interaction between the yeast and clay, a nitrogen high pressurized gas stream was applied on each mounted sample before coating with Au/P.

Example 5

Semi-Industrial Scaling-Up of the Production of Yeast Cell Wall Cultivated with Clay Scaled-Up Yeast Culture.

A 150 L fermenter (ML-4100, New Brunswick Scientific Co., Inc., Edison, N.J., U.S.A.) was used to grow the yeast *Sacchromyces cerevisiae* (active dry yeast (ADY) from Fermin, Alltech Inc., Batch #609, Yeast count: $2.38 \times 10^{10}$ cells/g, Viability: 92.6%). The yeast inoculum was prepared by transferring 0.84 kg of fresh ADY Fermin to a pre-autoclaved (121° C. during 40 min) 19 L carboy with tubing, covered with a BioShield containing 7.5 L of water and that has been maintained after autoclaving at 30° C. in an incubator overnight. Two 19 L Food carboy, covered with a BioShield were prepared by adding 9 L of water, 6 kg of dextrose and a stir bar. After mixing and dissolution of the carbon source, the food media was autoclaved (121° C. during 40 min). A Nitrogen solution was prepared using 1 L sterile capped bottle containing 250 mL of deionized water, 120 g of diammonium phosphate adjusted to pH 4.0-4.1 with concentrated HCl. Two 1 L sterile capped bottle of Food Nitrogen were prepared by adding 700 mL of deionized water, 192 g of diammonium phosphate adjusted to pH 4.0-4.1 with concentrated HCl. A Base solution was prepared in a 19 L carboy with tubing, covered with a BioShield and containing 13.5 L of water, 1.5 L KOH. The tubing was then connected to a peristaltic pump. An anti foaming agent (Antifoam AES, 1:10) solution was prepared in a 19 L carboy with tubing, covered with a BioShield and containing 12 L of water, 3 L of antifoaming agent (Antifoam AES, 3 kg) and mixed. The tubing was then connected to a peristaltic pump. The 150 L fermentor media was composed of 1.98 kg amber, 0.3 kg of peptone, 0.12 kg of dextrose, 0.12 kg of yeast nitrogen base, 0.516 g of smectite clay (American Colloid Company, Arlighton Height, Ill., USA) and 60 L of water that was brought to 121° C., 15 psi for 1 h with agitation. The medium was cooled down to 30° C. and this temperature was maintained throughout the propagation.

The propagation was performed on the 150 L fermenter maintained at 30° C. with mild agitation (70% of power) and air injection (at 5 psi) prior inoculation and during entire fermentation. The inoculum containing 0.84 kg of ADY in 7.5 L of water was stirred for 20-30 min prior to inoculation in the 150 L Fermentor. One bottle of Food Nitrogen was added to each Food carboy under mixing. The Nitrogen solution was pumped into the 150 L fermentor and allowed to mix for a minimum of 10 min prior to inoculation. The antifoam Carboy was attached and the anti-foaming agent pumped through the tubing into the 150 L fermentor as needed. A foam probe was set inside the fermentor to monitor the foaming and to allow supplementing correctly with the anti-foaming agent. The Base solution was attached and pumped through the tubing into the 150 L fermentor as needed. The evolution of the pH of the 150 L fermentor media was monitored and maintained at a minimum of pH 5.0 during the entire growth. The inoculation was performed by attaching the inoculum Carboy to the port and by pumping the content into the 150 L fermentor. Mixing of the inoculum in the fermentor was done for 20-30 min prior to first sampling. The foam was monitored throughout the propagation, adjusting air and agitation up hourly. The pH was monitored internally and externally and adjusted as necessary to maintain a pH of 5.0 or higher. The glucose level was tested during growth with diabetic strips (OneTouch, UltraMini, LifeScan, Inc., Milpitas, Calif., U.S.A.) and supplemental glucose was added when glucose level fell below 0.8 mg/mL by slowly pumping in the Food solution or speeding up gradually overtime. If the sugar level rose above 0.8 mg/mL, the feed rate was slowed down or shut off if necessary.

Yeast cultures were harvested when all sugar had been utilized. The content of the 150 L fermenter was collected into sterile bottles and centrifuged at 4000 g for 20 min. The supernatant was removed and the percentage of dry matter of the washed yeast measured. The material was then transferred back to the 150 L fermenter and water was added to bring the slurry from 9-11% to a concentration 13-15% of dry matter. Agitation was maintained at all times.

Clay Interlaced Yeast Cell Wall Extraction Through Enzyme Hydrolysis.

The 13-15% of dry matter yeast slurry was stirred at 60° C. The pH was adjusted using 10% NaOH to 8.0 before adding enzyme at 0.3 mL/L. The temperature and stirring conditions were maintained over 8 h. The pH was monitored and adjusted every 15 min (using the 10% NaOH) for the first two hours, and then the pH was monitored and adjusted every hour for the next six hours. The slurry was transferred to sterile centrifuge bottles and centrifuged at 4000 g for 20 min. The supernatant was discarded and the pellet washed with three volume of cold sterile water, and then centrifuged again at 4000 g for 20 min. The washing step was repeated two times before the pellet was frozen, freeze dried and ground. The increase of the temperature during the spray drying phase resulted in a slightly higher yield and less accumulation of product in the spray drier.

The inclusion of the clay material can be followed by the change in the ash concentration of the sample reaching values around 20% for the clay interlaced yeast cell wall compared to a 5% concentration in a yeast cell wall extract that is not containing any clay material (See, e.g. FIG. 6). A significant difference in terms of composition between the ADY Fermin yeast cell line produced previously in the Bioflow fermenters compared to the 150 L fermenter was also found with a decrease of the glucan and mannan composition in the large scale production but also an increase of the chitin content of the yeast cell wall (1.5% to 3%) accounting for the responses by the yeast cell wall to perturbing agent and implicating the cell wall signaling pathway.

Semi-industrial scale clay interlaced yeast cell wall extract products were evaluated for sequestration efficacy of mycotoxins (See, e.g. FIG. 7), and the results confirm increase of mycotoxin adsorption capabilities of clay interlaced yeast cell wall extracts.

Example 6

Production of Clay Interlaced Yeast Cell Wall Utilizing an Industrial Source of Sugar Yeast Culture.

*Sacchromyces cerevisiae* (active dry yeast (ADY) from Fermin, Alltech Inc., Yeast count: $2.38 \times 10^{10}$ cells/g, Viability: 92.6%) were grown in a Bioflow fermenter (BioFlow III, New Brunswick Scientific Co., Inc., Edison, N.J., U.S.A.). The yeast inoculum was prepared by transferring 29 g of fresh ADY Fermin to a pre-warmed bottle of 87 ml sterile deionized water. Then, the solution was incubated at 30° C. (in water bath) for 20 min and swirled several times. The BioFlow media was composed of 0.048 g calcium hipochloride, 0.24 g magnesium sulphate, 0.168 g zinc sulphate, 0.24 g magnesium chloride, 2.4 g (2.5 mL of prepared food) sugar cane must, 7.5 g smectite clay (0.5% in the final media, (American Colloid Company, Arlighton Height, Ill., USA)) and 1440 mL of deionized water. The sugar cane must is a 30% of total reducing sugars (TRS) solution of molasses diluted with water. Preparation of the must was made with 669 g of molasses (62.8% TRS) and 731 mL of deionized water. A nitrogen source was prepared with 54.5 g of urea in 163.5 mL of deionized water.

The Bioflow reactor media was warmed up at 30° C. and air was injected at 1 L/min flow rate during 10 min prior inoculation. Agitation was set at 300 rpm and the media monitored and maintained at a minimum of pH 5.0 during the entire growth using phosphoric acid, 85%. An anti-foaming agent was added (Antifoam AES, 1:10, as needed). The previously re-suspended yeast was added to the fermentor. The glucose level was tested during growth with diabetic stripes (OneTouch, UltraMini, LifeScan, Inc., Milpitas, Calif., U.S.A.) and supplemental food (from the sugar cane must) was added when glucose level fell below 0.8 mg/mL. The agitation was progressively increased to 500 rpm over 2 h of incubation as well as the air flow (up to 4 L/min over 3 h). The final concentration of clay to the reactor was 0.5% in the final media.

The amount of molasses to be added to the fermenter depended on the efficiency of the yeast to utilize the sugar and was comprised between 400 and 600 g. Overfeeding of molasses encountered production issues resulting in the incapacity to generate any yeast biomass through fermentation. Yeast cultures were harvested when no further growth was observed. The content of the BioFlow was collected into sterile bottles and centrifuged at 4000 g for 20 min. The supernatant was removed and the pellet was washed with 0.125% NaCl in $H_2O$. No separate fraction was found when molasses were used to perform the propagation of the yeast. Yeasts were then washed three times with 0.125% NaCl solution.

Clay Interlaced Yeast Cell Wall Extraction Method.

The yeast pellet was resuspended with sterile deionized water to a concentration of 13 to 15% of dry matter. The yeast slurry was stirred at 60° C. The pH was adjusted using 10% NaOH to 8.0 before adding enzyme at 0.3 mL/L. The temperature and stirring conditions were maintained over 8 h. The pH was monitored and adjusted every 15 min (using the 10% NaOH) for the first two hours, and then the pH was monitored and adjusted every hour for the next six hours. The slurry was transferred to sterile centrifuge bottles and centrifuged at 4000 g for 20 min. The supernatant was discarded and the pellet washed with three volume of cold sterile water, and then centrifuged again at 4000 g for 20 min. The washing step was repeated two times before the pellet was frozen, freeze dried and ground.

The sequestration efficacy of the produced material exhibited also differences according to the carbon source used to propagate the yeast (See, e.g. FIG. 8). The variations observed in terms of efficacy were also related to the type of mycotoxin considered. The composition of the material was also different from the composition of the material previously produced with dextrose as sole source of carbon. Levels of 13.4% of glucan; 17.8% of mannan; and 2.7% of chitin (N-acetyl-glucosamine) present in the yeast cell wall (and expressed by reference to the total cell) were found.

Example 7

In Vivo Efficacy Against *Fusarium* Mycotoxicoses

One-day-old Hybrid turkey poults (Hybrid Turkeys, Kitchener, ON, Canada) were individually weighed, wing-banded and distributed randomly into groups at the Arkell Poultry Research Station of the University of Guelph. Poults were randomly assigned to each of 5 diets. Poults were initially maintained at 32° C., and the temperature was gradually reduced by 3° C. per week to reach a temperature of 21° C. by the end of week 4. This temperature was maintained for the duration of the experiment. Turkey poults were fed corn, wheat and soybean meal-based starter (0-3 week), and grower (4-6 week) diets formulated with control grains, control +0.2% clay interlaced yeast cell wall, contaminated grains, and contaminated grains +0.2% clay interlaced yeast cell wall. The control diet was formulated to meet or exceed the minimum nutrient requirements of turkeys according to the NRC (1994). Mycotoxin-contaminated diets were prepared by replacing 25 and 10% and 26 and 5% of the control corn and wheat with contaminated corn and wheat naturally contaminated with *Fusarium* mycotoxins during starter and grower phases, respectively. The levels of replacement of control grains with the contaminated grains were calculated in order to achieve a mycotoxin challenge of about 4 mg DON/kg of diet during starter and grower phases. Clay interlaced yeast cell wall extract (abbrev. CIYCW in tables) supplemented diets were prepared by substituting control corn in the diets with 0.2% of clay interlaced yeast cell wall extract. Feed and water were provided ad libitum. Representative feed samples were taken at the beginning of each phase for proximate and mycotoxin analyses. Dietary contents of protein, dry matter and ash were determined according to the Association of Official Analytical Chemists (1980). The diet formulations and nutrient contents are presented in Table 1. The experimental procedures were approved by the University of Guelph Animal Care Committee following the guidelines of the Canadian Council on Animal Care.

TABLE 1

| Composition of experimental diets (%). | | | | |
|---|---|---|---|---|
| Ingredients | Control | Control + CIYCW | Contaminated | Contaminated + CIYCW |
| | Starter diet (0-3 wk) | | | |
| Corn | 36.00 | 35.80 | 11.02 | 10.82 |
| Contaminated corn | | | 24.98 | 24.98 |
| Wheat | 10.00 | 10.00 | | |
| Contaminated wheat | 0.00 | 0.00 | 10.00 | 10.00 |
| Soybean meal | 45.00 | 45.00 | 45.00 | 45.00 |
| Monocalcium phosphate | 2.30 | 2.30 | 2.30 | 2.30 |
| Calcium carbonate | 1.84 | 1.84 | 1.84 | 1.84 |
| Fat/Tallow | 3.00 | 3.00 | 3.00 | 3.00 |
| Salt | 0.40 | 0.40 | 0.40 | 0.40 |
| DL-Methionine | 0.22 | 0.22 | 0.22 | 0.22 |
| HCl-Lysine | 0.15 | 0.15 | 0.15 | 0.15 |
| Vitamin and mineral premix[1] | 1.00 | 1.00 | 1.00 | 1.00 |
| Anticoccidial[2] | 0.10 | 0.10 | 0.10 | 0.10 |
| CIYCW | | 0.20 | | 0.20 |
| Calculated values | | | | |
| ME, kcal/kg | | | 2800 | |
| Crude Protein | | | 26.50 | |
| Lysine | | | 1.60 | |
| Methionine | | | 0.62 | |
| Calcium | | | 1.20 | |
| Available phosphorus | | | 0.60 | |
| Analyzed values | | | | |
| Crude protein | 26.41 | 24.97 | 27.75 | 26.70 |
| DM | 88.70 | 89.03 | 88.99 | 89.14 |
| Ash | 8.10 | 6.97 | 7.12 | 7.00 |

TABLE 1-continued

Composition of experimental diets (%).

| Ingredients | Control | Control + CIYCW | Contaminated | Contaminated + CIYCW |
|---|---|---|---|---|
| | | Grower diet (4-6 wk) | | |
| Corn | 42.68 | 42.48 | 16.86 | 16.66 |
| Contaminated corn | | | 25.82 | 25.82 |
| Wheat | 5.00 | 5.00 | | |
| Contaminated wheat | | | 5.00 | 5.00 |
| Soybean meal | 42.00 | 42.00 | 42.00 | 42.00 |
| Monocalcium phosphate | 2.20 | 2.20 | 2.20 | 2.20 |
| Calcium carbonate | 1.40 | 1.40 | 1.40 | 1.40 |
| Fat/Tallow | 5.00 | 5.00 | 5.00 | 5.00 |
| Salt | 0.40 | 0.40 | 0.40 | 0.40 |
| DL-Methionine | 0.16 | 0.16 | 0.16 | 0.16 |
| HCl-Lysine | 0.06 | 0.06 | 0.06 | 0.06 |
| Vitamin and mineral premix[1] | 1.00 | 1.00 | 1.00 | 1.00 |
| Anticoccidial[2] | 0.10 | 0.10 | 0.10 | 0.10 |
| CIYCW | | 0.20 | | 0.20 |
| Calculated values | | | | |
| ME, kcal/kg | | | 3050 | |
| Crude Protein | | | 23 | |
| Lysine | | | 1.36 | |
| Methionine | | | 0.5 | |
| Calcium | | | 1.1 | |
| Available phosphorus | | | 0.52 | |
| Analyzed values | | | | |
| Crude protein | 23.31 | 24.29 | 24.27 | 27.70 |
| DM | 89.30 | 88.99 | 88.54 | 88.38 |
| Ash | 6.33 | 6.39 | 6.73 | 6.75 |

[1]Vitamin-mineral mixture provided per kilogram of diet: vitamin A (all-trans-retinyl palmitate), 8,800 IU; cholecalciferol, 3,300 IU; vitamin E (all-rac-α-tocopheryl acetate), 40 IU; menadione, 3.3 mg; thiamin, 4.0 mg; riboflavin, 8.0 mg; pantothenic acid, 15.0 mg; niacin, 50 mg; pyridoxine, 3.3 mg; choline, 600 mg; folic acid, 1.0 mg; biotin, 220 μg; vitamin $B_{12}$, 12 μg; ethoxyquin, 120 mg; manganese, 70 mg; zinc, 70 mg; iron, 60 mg; copper, 10 mg; iodine, 1.0 mg; selenium, 0.3 mg.
[2]Monensin sodium, 10%.

Dietary concentrations of deoxynivalenol, 15-acetyl-deoxynivalenol, zearalenone, fumonisin and ochratoxin A are given in Table 2. Other mycotoxins were below the method detection limits which were 0.12 mg/kg for nivalenol, 0.05 mg/kg for 3-acetyl-deoxynivalenol, 0.07 mg/kg for neosolaniol, 0.06 mg/kg for diacetoxyscirpenol and T-2 toxin and 0.04 mg/kg for HT-2 toxin, and 0.001 mg/kg for aflatoxins. The detection limits for deoxynivalenol, 15-acetyl-deoxynivalenol, zearalenone, fumonisin and ochratoxin A were 0.06, 0.05, 0.025, 0.05 and 0.0003 mg/kg, respectively.

The feeding of contaminated grains did not significantly affect the body weight gain, feed consumption and efficiency of feed utilization at the end of starter phase (Table 3). Feeding contaminated diet significantly increased the body weight gain and improved the feed efficiency compared to control at the end of grower phase. There was no effect of the diet on the feed intake during grower phase (Table 3). At the end of grower phase, supplementation of clay interlaced yeast cell wall extract to the contaminated diets increased the body weight gain, feed consumption and improved the efficiency of

TABLE 2

Mycotoxin concentrations (μg/g) in experimental diets.

| | Mycotoxin[1] | | | | |
|---|---|---|---|---|---|
| Diet | Deoxynivalenol | 15-acetyl-deoxynivalenol | Zearalenone | Fumonisin | Ochratoxin A |
| | | Starter (0-3 wk) | | | |
| Control | 0.44 | 0.055 | <0.025 | BDL[2] | 0.46 |
| Control + CIYCW | 0.53 | 0.087 | <0.025 | BDL | 0.79 |
| Contaminated | 3.3 | 0.17 | 0.35 | 56 | BDL |
| Contaminated + CIYCW | 4.1 | 0.17 | 0.47 | BDL | BDL |
| | | Grower (4-6 wk) | | | |
| Control | 0.44 | 0.12 | BDL | BDL | 0.62 |
| Control + CIYCW | 0.37 | 0.12 | BDL | BDL | 0.71 |
| Contaminated | 3.7 | 0.29 | 0.34 | 61 | 1.0 |
| Contaminated + CIYCW | 3.2 | 0.28 | 0.27 | 63 | 0.35 |

[1]Other mycotoxins, including diacetoxyscirpenol, T-2 toxin, nivalenol, 3-acetyl-DON, neosolaniol, HT-2 toxin, and aflatoxins were also measured in the experimental diets, but were not detected.
[2]Below detection limit.

feed utilization compared to control. Body weight gain and feed efficiency over 6 week experimental period were significantly higher in the birds fed contaminated diets and contaminated diets supplemented with clay interlaced yeast cell wall extract.

TABLE 3

Effect of dietary *Fusarium* mycotoxins on turkey performance[1]

| Diet | 0-3 wk | 4-6 wk | 0-6 wk |
|---|---|---|---|
| | Body weight gain (g/bird) | | |
| Control | 474.50 | 1420.81 | 1895.32 |
| Control + CIYCW | 501.45 | 1461.74 | 1963.19 |
| Contaminated | 511.93 | 1572.97 | 2084.90 |
| Contaminated + CIYCW | 502.00 | 1627.63 | 2129.64 |
| SEM | 15.35 | 29.48 | 37.59 |
| Control vs. Control + CIYCW | NS[2] | NS | NS |
| Control vs. Contaminated | NS | 0.0023 | 0.002 |
| Control vs. Contaminated + CIYCW | NS | 0.0002 | 0.0004 |
| Contaminated vs. Contaminated + CIYCW | NS | NS | NS |
| | Feed intake (g/bird/day) | | |
| Control | 32.44 | 117.85 | 75.14 |
| Control + CIYCW | 33.54 | 116.87 | 75.20 |
| Contaminated | 33.75 | 119.86 | 76.81 |
| Contaminated + CIYCW | 33.87 | 124.40 | 79.13 |
| SEM | 0.91 | 2.21 | 1.40 |
| Control vs. Control + CIYCW | NS | NS | NS |
| Control vs. Contaminated | NS | NS | NS |
| Control vs. Contaminated + CIYCW | NS | 0.05 | NS |
| Contaminated vs. Contaminated + CIYCW | NS | NS | NS |
| | Feed efficiency (body weight gain/feed intake) | | |
| Control | 0.69 | 0.57 | 0.60 |
| Control + CIYCW | 0.71 | 0.59 | 0.62 |
| Contaminated | 0.71 | 0.61 | 0.63 |
| Contaminated + CIYCW | 0.71 | 0.62 | 0.64 |
| SEM | 0.01 | 0.008 | 0.008 |
| Control vs. Control + CIYCW | NS | NS | NS |
| Control vs. Contaminated | NS | 0.0027 | 0.004 |
| Control vs. Contaminated + CIYCW | NS | 0.0007 | 0.001 |
| Contaminated vs. Contaminated + CIYCW | NS | NS | NS |

[1]Values are least square means; n = 4 pens for body weight gain, feed intake and feed efficiency (7-8 birds/pen/phase).
[2]p > 0.05

The feeding of contaminated grains increased (P<0.05) eosinophil counts at week 6 (Table 4). Supplementation of the contaminated diets with clay interlaced yeast cell wall extract prevented this. Supplementation of clay interlaced yeast cell wall extract to the control diet significantly increased the hematocrit compared to un-supplemented control. There was a significant reduction in the concentration of glucose and activities of γ-glutamyl transferase in the birds fed contaminated diet at week 3 compared to control (Table 5). Supplementation of clay interlaced yeast cell wall extract prevented this. Clay interlaced yeast cell wall extract supplementation to the contaminated diets significantly increased the concentrations of uric acid compared to control at week 3 and 6. There was a significant decrease in the activity of lactate dehydrogenase at week 3 in the birds fed contaminated diet+ clay interlaced yeast cell wall extract compared to control.

TABLE 4

Effect of dietary *Fusarium* mycotoxins on hematology[1]

| Diet | 3 wk | 6 wk |
|---|---|---|
| | Hemoglobin (g/L) | |
| Control | 93.50 | 105.88 |
| Control + CIYCW | 98.12 | 107.88 |
| Contaminated | 93.50 | 109.75 |
| Contaminated + CIYCW | 95.87 | 106.38 |
| SEM | 2.27 | 1.80 |
| Control vs.. Control + CIYCW | NS[2] | NS |
| Control vs. Contaminated | NS | NS |
| Control vs. Contaminated + CIYCW | NS | NS |
| | Hematocrit (L/L) | |
| Control | 0.30 | 0.31 |
| Control + CIYCW | 0.32 | 0.31 |
| Contaminated | 0.30 | 0.32 |
| Contaminated + CIYCW | 0.30 | 0.32 |
| SEM | 0.005 | 0.007 |
| Control vs. Control + CIYCW | 0.05 | NS |
| Control vs. Contaminated | NS | NS |
| Control vs. Contaminated + CIYCW | NS | NS |
| | MCHC (g/L) | |
| Control | 302.80 | 335.38 |
| Control + CIYCW | 300.88 | 345.25 |
| Contaminated | 303.13 | 336.13 |
| Contaminated + CIYCW | 310.88 | 331.63 |
| SEM | 5.44 | 5.52 |
| Control vs. Control + CIYCW | NS | NS |
| Control vs. Contaminated | NS | NS |
| Control vs. Contaminated + CIYCW | NS | NS |
| | WBC ($10^9$/L) | |
| Control | 15.37 | 16.75 |
| Control + CIYCW | 18.71 | 16.75 |
| Contaminated | 17.96 | 16.07 |
| Contaminated + CIYCW | 18.93 | 19.96 |
| SEM | 1.93 | 2.26 |
| Control vs. Control + CIYCW | NS | NS |
| Control vs. Contaminated | NS | NS |
| Control vs. Contaminated + CIYCW | NS | NS |
| | Heterophils ($10^9$/L) | |
| Control | 6.20 | 9.37 |
| Control + CIYCW | 8.36 | 9.19 |
| Contaminated | 7.98 | 8.71 |
| Contaminated + CIYCW | 7.86 | 10.36 |
| SEM | 0.93 | 1.26 |
| Control vs. Control + CIYCW | NS | NS |
| Control vs. Contaminated | NS | NS |
| Control vs. Contaminated + CIYCW | NS | NS |
| | Lymphocytes ($10^9$/L) | |
| Control | 7.37 | 5.54 |
| Control + CIYCW | 8.00 | 5.61 |
| Contaminated | 8.60 | 5.48 |
| Contaminated + CIYCW | 8.92 | 8.54 |
| SEM | 1.22 | 1.29 |
| Control vs. Control + CIYCW | NS | NS |
| Control vs. Contaminated | NS | NS |
| Control vs. Contaminated + CIYCW | NS | NS |
| | Monocytes ($10^9$/L) | |
| Control | 0.71 | 0.52 |
| Control + CIYCW | 1.30 | 0.65 |
| Contaminated | 0.56 | 0.75 |
| Contaminated + CIYCW | 0.93 | 0.25 |
| SEM | 0.29 | 0.22 |
| Control vs. Control + CIYCW | NS | NS |
| Control vs. Contaminated | NS | NS |
| Control vs. Contaminated + CIYCW | NS | NS |
| | Eosinophils ($10^9$/L) | |
| Control | 0.27 | 0.15 |
| Control + CIYCW | 0.38 | 0.34 |
| Contaminated | 0.34 | 0.38 |
| Contaminated + CIYCW | 0.33 | 0.06 |

TABLE 4-continued

Effect of dietary Fusarium mycotoxins on hematology[1]

| Diet | 3 wk | 6 wk |
|---|---|---|
| SEM | 0.11 | 0.079 |
| Control vs. Control + CIYCW | NS | NS |
| Control vs. Contaminated | NS | 0.04 |
| Control vs. Contaminated + CIYCW | NS | NS |
| Basophils ($10^9$/L) | | |
| Control | 0.79 | 0.61 |
| Control + CIYCW | 0.65 | 0.89 |
| Contaminated | 0.47 | 0.74 |
| Contaminated + CIYCW | 0.87 | 0.71 |
| SEM | 0.19 | 0.18 |
| Control vs. Control + CIYCW | NS | NS |
| Control vs. Contaminated | NS | NS |
| Control vs. Contaminated + CIYCW | NS | NS |

[1]Values are least square means; for each diet and phase n = 4 pens and 2 birds per pen.
[2]P > 0.05

TABLE 5

Effect of dietary Fusarium mycotoxins on plasma chemistry[1]

| Diet | 3 wk | 6 wk |
|---|---|---|
| Calcium (mmol/L) | | |
| Control | 3.05 | 2.94 |
| Control + CIYCW | 3.15 | 2.97 |
| Contaminated | 3.05 | 3.03 |
| Contaminated + CIYCW | 3.13 | 3.14 |
| SEM | 0.04 | 0.04 |
| Control vs. Control + CIYCW | NS[2] | NS |
| Control vs. Contaminated | NS | NS |
| Control vs. Contaminated + CIYCW | NS | 0.002 |
| Phosphorus (mmol/L) | | |
| Control | 2.57 | 2.46 |
| Control + CIYCW | 2.59 | 2.44 |
| Contaminated | 2.67 | 2.47 |
| Contaminated + CIYCW | 2.64 | 2.64 |
| SEM | 0.08 | 0.06 |
| Control vs. Control + CIYCW | NS | NS |
| Control vs. Contaminated | NS | NS |
| Control vs. Contaminated + CIYCW | NS | 0.05 |
| Total Protein (g/L) | | |
| Control | 29.12 | 31.25 |
| Control + CIYCW | 30.12 | 31.12 |
| Contaminated | 29.62 | 32.62 |
| Contaminated + CIYCW | 29.75 | 34.25 |
| SEM | 0.52 | 0.68 |
| Control vs. Control + CIYCW | NS | NS |
| Control vs. Contaminated | NS | NS |
| Control vs. Contaminated + CIYCW | NS | 0.003 |
| Albumin (g/L) | | |
| Control | 8.37 | 8.37 |
| Control + CIYCW | 8.12 | 8.62 |
| Contaminated | 8.25 | 8.50 |
| Contaminated + CIYCW | 8.75 | 9.00 |
| SEM | 0.29 | 0.25 |
| Control vs. Control + CIYCW | NS | NS |
| Control vs. Contaminated | NS | NS |
| Control vs. Contaminated + CIYCW | NS | NS |
| Globulin (g/L) | | |
| Control | 20.75 | 22.87 |
| Control + CIYCW | 22.00 | 22.50 |
| Contaminated | 21.37 | 24.12 |
| Contaminated + CIYCW | 21.00 | 25.25 |
| SEM | 0.55 | 0.57 |
| Control vs. Control + CIYCW | NS | NS |
| Control vs. Contaminated | NS | NS |
| Control vs. Contaminated + CIYCW | NS | 0.006 |
| Albumin:Globulin ratio | | |
| Control | 0.40 | 0.36 |
| Control + CIYCW | 0.37 | 0.38 |
| Contaminated | 0.38 | 0.35 |
| Contaminated + CIYCW | 0.42 | 0.35 |
| SEM | 0.01 | 0.01 |
| Control vs. Control + CIYCW | NS | NS |
| Control vs. Contaminated | NS | NS |
| Control vs. Contaminated + CIYCW | NS | NS |
| Glucose (mmol/L) | | |
| Control | 18.35 | 17.82 |
| Control + CIYCW | 18.13 | 17.45 |
| Contaminated | 17.31 | 17.52 |
| Contaminated + CIYCW | 17.63 | 17.23 |
| SEM | 0.37 | 0.34 |
| Control vs. Control + CIYCW | NS | NS |
| Control vs. Contaminated | 0.05 | NS |
| Control vs. Contaminated + CIYCW | NS | NS |
| Cholesterol (mmol/L) | | |
| Control | 4.12 | 4.17 |
| Control + CIYCW | 3.99 | 4.23 |
| Contaminated | 4.10 | 4.04 |
| Contaminated + CIYCW | 4.03 | 3.73 |
| SEM | 0.12 | 0.13 |
| Control vs. Control + CIYCW | NS | NS |
| Control vs. Contaminated | NS | NS |
| Control vs. Contaminated + CIYCW | NS | 0.02 |
| Total Bilirubin (umol/L) | | |
| Control | 5.37 | 2.37 |
| Control + CIYCW | 5.87 | 2.37 |
| Contaminated | 4.87 | 2.12 |
| Contaminated + CIYCW | 5.12 | 2.62 |
| SEM | 0.70 | 0.38 |
| Control vs. Control + CIYCW | NS | NS |
| Control vs. Contaminated | NS | NS |
| Control vs. Contaminated + CIYCW | NS | NS |
| γ-glutamyl-transferase (U/L) | | |
| Control | 1.75 | 1.75 |
| Control + CIYCW | 2.00 | 1.50 |
| Contaminated | 0.75 | 1.87 |
| Contaminated + CIYCW | 0.87 | 1.00 |
| SEM | 0.33 | 0.18 |
| Control vs. Control + CIYCW | NS | NS |
| Control vs. Contaminated | 0.04 | NS |
| Control vs. Contaminated + CIYCW | NS | 0.008 |
| Aspartate aminotransferase (U/L) | | |
| Control | 211.38 | 212.63 |
| Control + CIYCW | 226.25 | 207.75 |
| Contaminated | 226.75 | 211.63 |
| Contaminated + CIYCW | 205.00 | 203.75 |
| SEM | 8.15 | 6.42 |
| Control vs. Control + CIYCW | NS | NS |
| Control vs. Contaminated | NS | NS |
| Control vs. Contaminated + CIYCW | NS | NS |
| Creatine Kinase (U/L) | | |
| Control | 1352.63 | 1047.13 |
| Control + CIYCW | 1309.38 | 907.63 |
| Contaminated | 1649.25 | 953.38 |
| Contaminated + CIYCW | 1147.00 | 1086.63 |
| SEM | 173.46 | 145.41 |
| Control vs. Control + CIYCW | NS | NS |
| Control vs. Contaminated | NS | NS |
| Control vs. Contaminated + CIYCW | NS | NS |
| Amylase (U/L) | | |
| Control | 809.63 | 877.38 |
| Control + CIYCW | 821.63 | 764.88 |
| Contaminated | 872.50 | 913.25 |
| Contaminated + CIYCW | 891.38 | 902.88 |

TABLE 5-continued

Effect of dietary *Fusarium* mycotoxins on plasma chemistry[1]

| Diet | 3 wk | 6 wk |
|---|---|---|
| SEM | 57.27 | 54.54 |
| Control vs. Control + ClYCW | NS | NS |
| Control vs. Contaminated | NS | NS |
| Control vs. Contaminated + ClYCW | NS | NS |
| Lipase (U/L) | | |
| Control | 5.37 | 2.87 |
| Control + ClYCW | 4.37 | 4.50 |
| Contaminated | 4.75 | 3.62 |
| Contaminated + ClYCW | 5.87 | 4.25 |
| SEM | 0.94 | 0.72 |
| Control vs. Control + ClYCW | NS | NS |
| Control vs. Contaminated | NS | NS |
| Control vs. Contaminated + ClYCW | NS | NS |
| Uric acid (U/L) | | |
| Control | 247.75 | 167.13 |
| Control + ClYCW | 221.50 | 144.38 |
| Contaminated | 292.50 | 164.75 |
| Contaminated + ClYCW | 334.50 | 279.00 |
| SEM | 28.23 | 24.77 |
| Control vs. Control + ClYCW | NS | NS |
| Control vs. Contaminated | NS | NS |
| Control vs. Contaminated + ClYCW | 0.03 | 0.003 |
| Lactate dehydrogenase (U/L) | | |
| Control | 664.88 | 531.00 |
| Control + ClYCW | 661.75 | 542.13 |
| Contaminated | 646.63 | 469.25 |
| Contaminated + ClYCW | 566.13 | 497.63 |
| SEM | 30.24 | 20.84 |
| Control vs. Control + ClYCW | NS | NS |
| Control vs. Contaminated | NS | 0.04 |
| Control vs. Contaminated + ClYCW | 0.02 | NS |
| Glutamate dehydrogenase (U/L) | | |
| Control | 4.62 | 2.87 |
| Control + ClYCW | 3.25 | 2.62 |
| Contaminated | 4.25 | 2.37 |
| Contaminated + ClYCW | 3.50 | 2.50 |
| SEM | 0.70 | 0.36 |
| Control vs. Control + ClYCW | NS | NS |
| Control vs. Contaminated | NS | NS |
| Control vs. Contaminated + ClYCW | NS | NS |

[1]Values are least square means; for each diet and phase n = 4 pens and 2 birds per pen.
[2]$P > 0.05$ The feeding of contaminated grains significantly decreased the activities of lactate dehydrogenase at week 6 compared to control (Table 5). Supplementation of clay interlaced yeast cell wall extract prevented this. There was a significant increase in the concentrations of calcium and phosphorus in the birds fed contaminated and clay interlaced yeast cell wall extract diet compared to control at week 6. The same diet at week 6 also significantly decreased the activities of γ-glutamyl transferase compared to control. A significant increase in the concentrations of total protein and globulin, and decrease in cholesterol levels were observed in the birds fed contaminated diet when supplemented with clay interlaced yeast cell wall extract.

The feeding of grains naturally contaminated with *Fusarium* mycotoxins to turkeys resulted in a hormetic response with respect to body weight gain and feed efficiency. Feed-borne *Fusarium* mycotoxins resulted in some effects on blood parameters compared to controls including increased eosinophil counts and decreased lactate dehydrogenase activities at week 6 and decreased glucose concentrations and gamma-glutamyl transferase activity at week 3. The feeding of clay interlaced yeast cell wall extract prevented all of these effects. The feeding of clay interlaced yeast cell wall extract resulted in numerical increases ($P > 0.05$) in growth compared to the feeding of unsupplemented contaminated grains.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

What is claimed is:

1. A method of reducing bioavailability of mycotoxins in a feedstuff consumed by an animal or human comprising:
   incorporating a clay interlaced yeast cell wall extract into the feedstuff, wherein the clay interlaced yeast cell wall extract is prepared by:
   (a) cultivating yeast in the presence of clay to form a clay interlaced yeast; and
   (b) extracting the clay interlaced yeast under suitable conditions to obtain the clay interlaced yeast cell wall extract.

2. The method of claim 1, wherein about 0.0125% to about 0.4% of said clay interlaced yeast cell wall extract is added by weight to said feedstuff.

3. The method of claim 1, wherein said animal is selected from the group consisting of avian, bovine, porcine, equine, ovine, caprine, piscines, shellfish, camelids, feline, canine and rodent species.

4. The method of claim 1, wherein feedstuff is selected from the group consisting of a Total Mixed Ration (TMR), a forage, a pellet, a concentrate, a premix, grain, distiller grain, molasses, fiber, fodder, grass, hay, kernel, leaves, meal, distiller solubles and a feed supplement.

5. The method of claim 1, further comprising incorporating an additional agent into said clay interlaced yeast cell wall extract incorporated feedstuff, wherein said agent is selected from the group consisting of an esterase and an epoxidase.

6. A method of feeding an animal or human a feedstuff containing a reduced bioavailablity of mycotoxin therein, the method comprising administering to the animal or human a feedstuff containing clay interlaced yeast cell wall extract, wherein the clay interlaced yeast cell wall extract is prepared by:
   (a) cultivating yeast in the presence of clay to form a clay interlaced yeast; and
   (b) extracting the clay interlaced yeast under suitable conditions to obtain the clay interlaced yeast cell wall extract.

7. The method of claim 6, wherein said feedstuff selected from the group consisting of a Total Mixed Ration (TMR), a forage, a pellet, a concentrate, a premix, grain, distiller grain, molasses, fiber, fodder, grass, hay, kernel, leaves, meal, distiller solubles and a feed supplement.

* * * * *